United States Patent [19]

Bourgery et al.

[11] 4,248,788

[45] Feb. 3, 1981

[54] SUBSTITUTED BENZODIOXANE, BENZODIOXOLE AND BENZODIOXEPINE COMPOUNDS

[75] Inventors: Guy R. Bourgery, Colombes; Alain P. Lacour, La Varenne; Gerard H. Moinet, Orsay; Bernard M. Pourrias, La Foret; Anne-Marie P. Ruch, Paris, all of France

[73] Assignee: Delalande S.A., Courbevoie, France

[21] Appl. No.: 29,653

[22] Filed: Apr. 13, 1979

Related U.S. Application Data

[63] Continuation-in-part of Ser. No. 894,965, Apr. 10, 1978, Pat. No. 4,178,442.

[30] Foreign Application Priority Data

Apr. 19, 1977 [FR] France .............................. 77 11707

[51] Int. Cl.³ .................. C07D 319/18; C07D 317/64

[52] U.S. Cl. .................. 260/340.3; 260/340.5 R; 544/148

[58] Field of Search .............. 544/148; 260/340.3, 260/340.5 R

[56] References Cited

U.S. PATENT DOCUMENTS 2,699,438   1/1955   Bock et al. ..................... 260/340.3

Primary Examiner—Henry R. Jiles
Assistant Examiner—R. W. Ramsuer
Attorney, Agent, or Firm—Blanchard, Flynn, Thiel, Boutell & Tanis

[57] ABSTRACT

Alcohol, thiol, epoxylated alcohol, epoxylated thiol and benzyloxy derivatives of benzodioxane, benzodioxole and benzodioxepine are useful as intermediates for preparing certain useful cinnamoyl piperazines and homopiperazines.

8 Claims, No Drawings

4,248,788

SUBSTITUTED BENZODIOXANE, BENZODIOXOLE AND BENZODIOXEPINE COMPOUNDS

CROSS REFERENCE TO RELATED APPLICATION

This application is a continuation-in-part of Ser. No. 894,965, filed Apr. 10, 1978 now U.S. Pat. No. 4,178,442.

This invention relates to compounds having the formula:

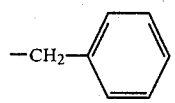

wherein:
I. R is

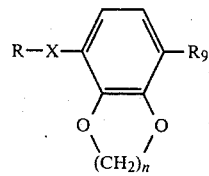

and the parameters (X,n) are:
A. (oxygen, 2) and $R_9$ is methoxy, acetoxy, methyl, cyano, acetyl, n-butyroyl, alkoxycarbonyl in which the alkyl group is linear or branched and has from 2 to 5 carbon atoms, cyclohexyloxycarbonyl, carboxamido, N-methylcarboxamido, N-cyclohexylcarboxamido, N-phenylcarboxamido, alkanoylamino in which the alkyl group is linear or branched and has 1 to 4 carbon atoms, cyclohexylcarbonylamino, benzoylamino, N-alkylcarbamoylamino in which the alkyl group is linear or branched and has from 1 to 5 carbon atoms, N-cyclohexylcarbamoylamino, N-phenylcarbamoylamino, N-(paramethoxyphenyl) carbamoylamino, N,N-dimethylcarbamoylamino, morpholinocarbonylamino, N,N'-dimethyl carbamoylamino, ethoxycarbonylamino, cyanomethyl, ethyl acetate, carboxamidomethyl or N-methylcarboxamidomethyl,
B. (oxygen, 1) or (oxygen, 3) and $R_9$ is acetyl, acetamido or N-methylcarbamoylamino,
C. (sulfur, 2) and $R_9$ is hydrogen or acetyl,
II. R is hydrogen and the parameters (X, n) are:
A. (oxygen, 2) and $R_9$ is acetoxy, cyano, methyl, n-butyroyl, alkoxycarbonyl in which the alkyl group is linear or branched and has from 2 to 5 carbon atoms, cyclohexyloxycarbonyl, carboxamido, N-methylcarboxamido, N-cyclohexylcarboxamido, N-phenylcarboxamido, alkanoylamino the alkyl group is linear or branched and has from 1 to 5 carbon atoms, cyclohexylcarbonylamino, benzoylamino, N-alkylcarbamoylamino the alkyl group of which is linear or branched and has from 1 to 5 carbon atoms, N-cyclohexylcarbamoylamino, N-phenylcarbamoylamino, N-paramethoxyphenylcarbamoylamino, N,N-dimethylcarbamoylamino, morpholinocarbonylamino, N,N'-dimethylcarbamoylamino, ethoxycarbonylamino, hydroxymethyl, cyanomethyl, ethyl acetate, carboxamidomethyl and N-methylcarboxamidomethyl and acetyl oxime,
B. (oxygen, 1), (oxygen, 3) and $R_9$ is acetyl, acetamido or N-methylcarbamoylamino,
C. (sulfur, 2) and $R_9$ is hydrogen or acetyl,
III. R is

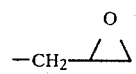

and the parameters (X, n) are:
A. (oxygen, 2) and $R_9$ is methoxy, acetyl, hydroxy, acetoxy, alkoxycarbonyl in which the alkyl group is linear or branched and has from 2 to 5 carbon atoms, cyclohexyloxycarbonyl, carboxamido, N-methylcarboxamido, N-cyclohexylcarboxamido, N-phenylcarboxamido, alkanoylamino the alkyl group of which is linear or branched and has from 2 to 5 carbon atoms, cyclohexylcarbonylamino, benzoylamino, N-alkylcarbamoylamino the alkyl group of which is linear or branched and has from 1 to 5 carbon atoms, N-cyclohexylcarbamoylamino, N-phenylcarbamoylamino, N-paramethoxyphenylcarbamoylamino, ethoxycarbonylamino, N,N'-dimethylcarbamoylamino, methylamino, morpholinocarbonylamino, N,N-dimethylcarbamoylamino, carboxamidomethyl, N-methylcarboxamidomethyl, hydroxycarbonylmethyl, cyano, ethyl acetate, carboxy, amino, hydroxymethyl, cyanomethyl, chloromethyl or acetamido,
B. (oxygen, 1) or (oxygen, 3) and $R_9$ is N-methylcarbamoylamino, acetyl, amino, acetamido or acetyloxime.

The compounds of the invention are useful as intermediates for preparing useful compounds having the following formula (I), as disclosed in U.S. Pat. application Ser. No. 894,965, filed Apr. 10, 1978 now U.S. Pat. No. 4,178,442, the entire contents of which are incorporated herein by reference.

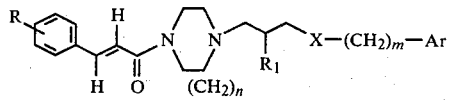

in which:

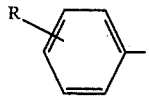

represents the 3,4,5 trimethoxyphenyl group

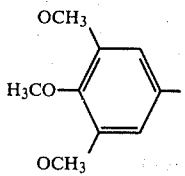

in which case the set of parameters (n, R, X, m) takes:

+either the value (1, OH, Oxygen, O), the radical AR then representing:
—a mono or polysubstituted phenyl nucleus:

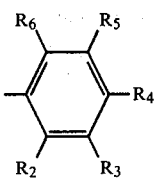

in which $R_2$, $R_3$, $R_4$, $R_5$ and $R_6$ represent simultaneously the following values;
- $R_3=R_4=R_5=R_6=H$; $R_2$ then represents either the atom of chlorine or fluorine or the acetamido, acetyl, cyano, methoxy, methyl, allyl or allyloxy groups,
- $R_2=R_4=R_5=R_6=H$; $R_3$ represents the acetamido, methyl, acetyl, cyano, methoxy groups or the atom of chlorine,
- $R_2=R_3=R_5=R_6=H$; $R_4$ represents the atom of chlorine or the cyano, nitro, methylthio, benzoyl, ethyl carboxylate, methyl groups, linear or branched alkyl possessing from 3 to 5 atoms of carbon, cyclohexyl, alkanoyl of which the alkyl has from 1 to 3 carbon atoms, alkanoylamino whose alkyl comprises from 1 to 3 carbon atoms, carboxamido or N-methyl carboxamido, or the cyanomethyl, carboxamidomethyl or N-methyl-carbamoylamino chains,
- $R_3=R_5=R_6H$; $R_2$ represents the atom of fluorine and $R_4$ represents the acetyl group,
- $R_3=R_5=R_6H$; $R_2$ represents the chlorine atom and $R_4$ represents either the nitro or acetyl groups, or the N-methyl carbamoyl amino chain;
- $R_3=R_5=R_6=H$; $R_2$ represents the methyl group and $R_4$ represents either the chlorine atom or the acetyl or acetamido groups or the N-methyl carbamoyl amino chain,
- $R_3=R_5=R_6H$; $R_2$ represents the methoxy group and $R_4$ represents the acetyl, propionyl, formyl, cyano, acetamido, or N-methyl carboxamido groups,
- $R_4=R_5=R_6=H$; $R_2$ and $R_3$ represent the methoxy group,
- $R_3=R_4=R_5=H$; $R_2$ and $R_6$ represent the methoxy group,
- $R_2=R_4=R_6=H$; $R_3$ and $R_5$ represent the methoxy group,
- $R_2=R_5=R_6=H$; $R_3$ and $R_4$ represent together methylene dioxy,
- $R_2=R_5=R_6=H$; $R_3$ represents the methyl group and $R_4$ represents the nitro, or acetamido groups or the N-methyl carbamoylamino chain,
- $R_2=R_6=H$; $R_3$, $R_4$ and $R_5$ represent the methoxy group,
- $R_2=R_6=H$; $R_3$ and $R_5$ represent the methyl group and $R_4$ represents the chlorine atom,
- $R_5=R_6=H$; $R_2$ and $R_3$ represent the methoxy group and $R_4$ the N-methyl carbamoyl amino group,
- $R_3=R_5=H$; $R_2$ and $R_6$ represent the chlorine atom and $R_4$ represents the acetyl group or the N-methyl carbamoyl amino chain,
- $R_3=R_5=H$; $R_2$ and $R_6$ represent the methoxy group and $R_4$ represents the acetyl, or ethyl carboxylate groups or the N-methyl carbamoyl amino chain,
- $R_5=H$; $R_3$, $R_4$ and $R_6$ represent the methoxy group and $R_2$ represents the acetyl group,
—a heterocycle of formula

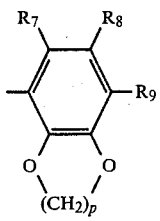

in which p, $R_7$, $R_8$ and $R_9$ represent simultaneously the following values,
- $p=2$; $R_7=R_8=H$; $R_9$ represents either the hydrogen atom or the hydroxy, acetoxy, methoxy, methyl, ethyl, cyano, acetyl, n-butyroyl, alkoxy carbonyl in which the alkyl is linear or branched and comprises from 2 to 5 carbon atoms, cyclohexyloxy carbonyl, carboxamido, N-methyl carboxamido, N-cyclohexyl carboxamido, N-phenyl-carboxamido groups, alkanoyl amino group whose linear or branched alkyl has from 1 to 5 carbon atoms, cyclohexylcarbonylamino, benzoylamino, N-alkylcarbamoylamino whose linear or branched alkyl has from 1 to 5 carbon atoms, N-cyclohexyl-carbamoylamino, N-phenylcarbamoylamino, N-(paramethoxy phenyl)-carbamoylamino, N,N-dimethylcarbamoylamino, morpholinocarbonylamino, N,N'-dimethylcarbamoylamino, ethoxy carbonylamino groups or the hydroxymethyl, cyanomethyl, ethyl acetate, carboxamido methyl or N-methyl carboxamido methyl chains,
- $p=2$; $R_7=R_9=H$; $R_8$ represents the acetyl group,
- $p=2$; $R_8=R_9=H$; $R_7$ represents the acetamido group,
- $p=1$ or 3; $R_7=R_8=H$; $R_9$ represents either the hydrogen atom or the acetyl, acetamido or N-methylcarbamoyl amino groups,
—a naphthalene nucleus of the type

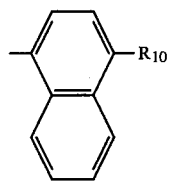

in which $R_{10}$ represents the acetyl, acetamido or N-methyl carbamoyl amino groups,
—a heterocycle of formula

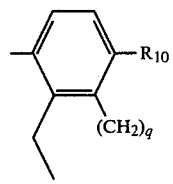

in which q assumes the values 1 or 2 and $R_{10}$ has the same meaning as previously,
—the groups (oxo-1, tetrahydro 1-2-3-4 naphtyl)-5 of formula

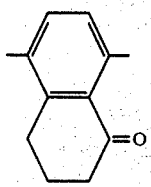

and (oxo-1, tetrahydro 1-2-3-4 naphtyl)-6 of formula

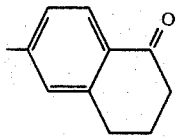

+or the value (2, OH, Oxygen, 0) the Ar radical then representing:
—either the phenyl group,
—or an aromatic group

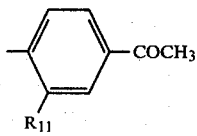

in which $R_{11}$ represents the hydrogen atom or the methoxy group,
—or a heterocycle

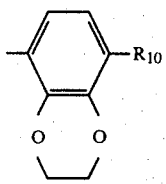

in which $R_{10}$ has the same meaning as previously,
+or the value (1, H, Oxygen, 0), the Ar radical then representing a heterocycle of the type

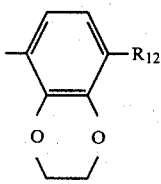

in which: $R_{12}$ represents the acetyl, acetamido, N-methyl carboxamido or N-methylcarbamoylamino groups,
+or the value (1, OH, S, 0), the Ar radical then representing:
—either the phenyl, meta-methoxyphenyl or paratolyl groups,
—or an aromatic group

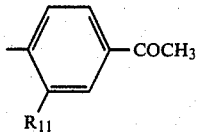

in which $R_{11}$ represents the hydrogen atom or the methoxy group,
—or a heterocycle

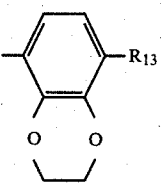

in which $R_{13}$ represents the hydrogen atom or the acetyl group,
+or the value $$(1, OH, -\underset{\underset{CH_3}{|}}{N}-, O)$$

the Ar radical then representing the phenyl group,
+or the value (1, OH, Oxygen, 1), the Ar radical then representing the phenyl group,

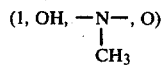

represents:
+either the 4-fluorophenyl, 3,5-dimethoxyphenyl or 3,4-methylenedioxyphenyl groups,
+or the aromatic groups

in which $R_{14}$ represents the hydrogen atom or a linear or branched alkyl having 2 to 3 carbon atoms in which case the set of parameters (n, $R_1$, X, m), assumes the value (1, OH, Oxygen, 0) and the Ar radical represents the

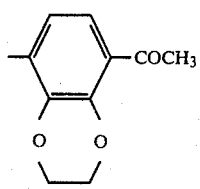

group

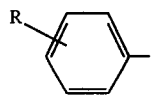

represents the group

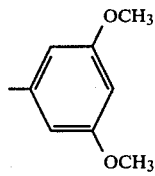

in which case the set of parameters (n, $R_1$, X, m) assumes the value (1, OH, Oxygen, 0) and Ar is

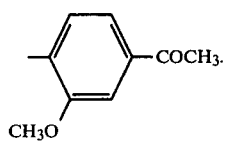

The process for preparing the compounds of formula (I), except for the 7 following compounds of formula (I):

• the compound of formula (I) in which

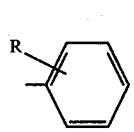 is 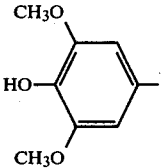

• the compound of formula (I) in which X represents the methylamino group

• the compound of formula (I) in which Ar is

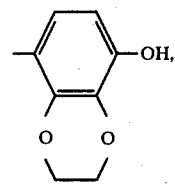

and

• the four compounds of formula (I) in which $R_1$ represents the hydrogen atom, consists in condensing a piperazine or a homopiperazine of formula (II)

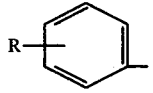

(II)

in which n assumes the values 1 and 2 and

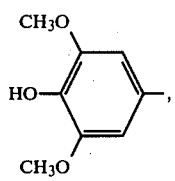

has the same meanings as

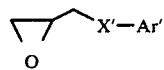

in formula (I) except for the value

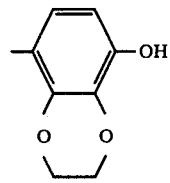

with an epoxy of formula (III):

$$\underset{O}{\triangle}\!\!-\!\!X'\!\!-\!\!Ar'$$ (III)

in which Ar' has the same meaning as Ar in formula (I), except for the value

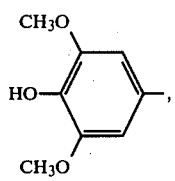

and X' represents the atom of oxygen or sulphur, or with epoxy-2,3 benzyloxy-1 propane, to obtain the compound of formula (I) in which m=1.

This condensation is carried out preferably in ethanol with reflux.

Following the same process as above, but from suitable reagents, the compound corresponding to formula (Ia):

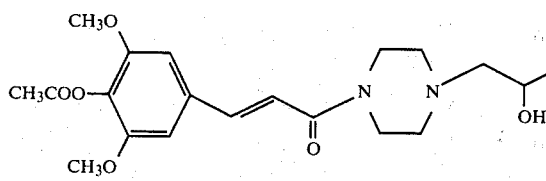 (Ia)

will be prepared.

The novel compounds of formula (II), particularly those corresponding to formulae (IIb) and (IIa).

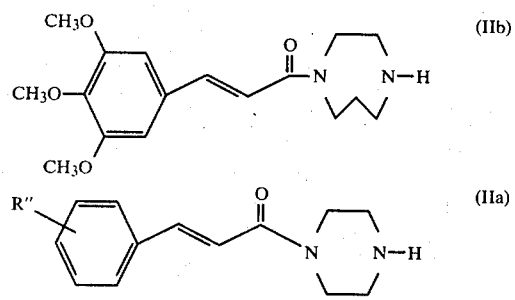

in which

represents the following aromatic groups

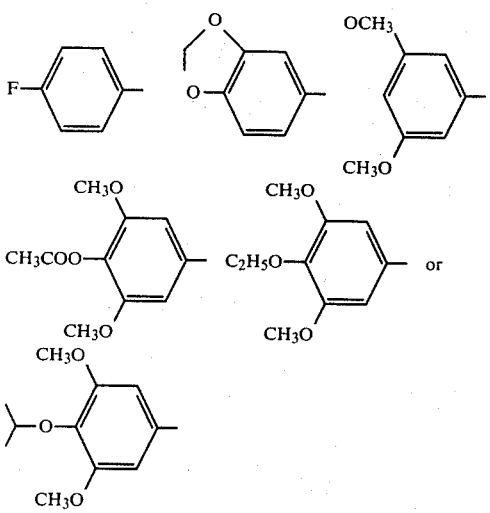

are obtained by condensation of the compounds of formulae (IV) and (IVa):

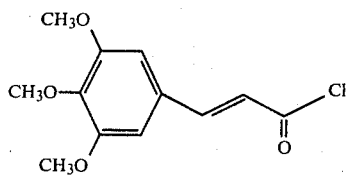 (IV)

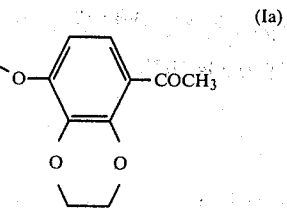 (IVa)

in which R" has the same meanings as in (IIa) respectively, with homopiperazine and piperazine. This condensation is carried out preferably in solution in acetic acid.

The compounds of formula (IVa), particularly those in which

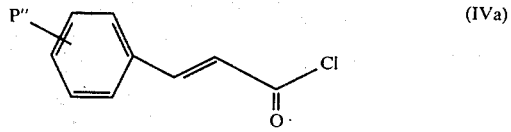

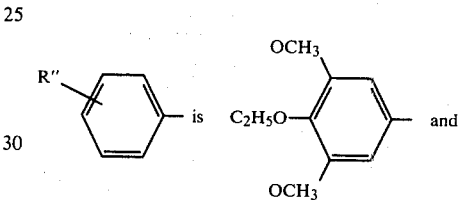

are obtained by action of thionyl chloride, in a toluene solution on corresponding cinnamoic acids of formula (V):

 (V)

in which $R'_{14}$ represents the ethyl and isopropyl groups.

The compounds (V) are obtained by saponification of the ethyl esters of the corresponding cinnamoic acids of formula (VI):

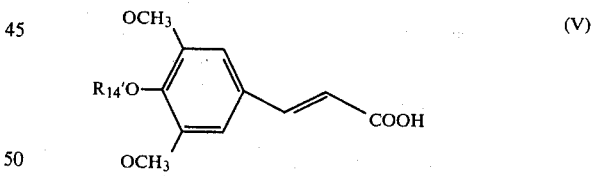 (VI)

in which $R'_{14}$ has the same meaning as in (V).

The compounds of formula (VI) were used in the crude state and are prepared by action of ethyl iodide or of isopropyl iodide on the ethyl ester of sinapic acid, in solution of acetonitrile and in the presence of potassium carbonate.

The compounds of formula (III):

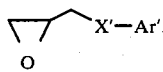

are partially novel and particularly those in which X' represents an oxygen atom and the Ar' radical represents:

(a) a mono or polysubstituted phenyl nucleus

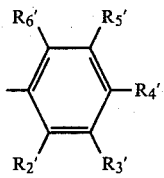

in which $R'_2$, $R'_3$, $R'_4$, $R'_5$ and $R'_6$ represent simultaneously the following values:
- $R'_3=R'_5=R'_6=H$; $R'_2=F$; $R'_4=COCH_3$
- $R'_3=R'_5=R'_6=H$; $R'_2=OCH_3$; $R'_4=COCH_3$, COEt
- $R'_3=R'_5=R'_6=H$; $R'_2=Cl$; $R'_4=COCH_3$, $NO_2$
- $R'_2=R'_5=R'_6=H$; $R'_3=CH_3$; $R'_4=NO_2$, NH-CONH-CH$_3$
- $R'_5=R'_6=H$; $R'_2=R'_3=OCH_3$; $R'_4=NHCONH-CH_3$
- $R'_3=R'_5=H$; $R'_2=R'_6=Cl$; $R'_4=COCH_3$, NY-CONHCH$_3$
- $R'_3=R'_5=H$; $R'_2=R'_6=OCH_3$; $R'_4=COCH_3$, COOEt, or NHCONHCH$_3$
- $R'_5=H$; $R'_3=R'_4=R'_6=OCH_3$; $R'_2=COCH_3$
- $R'_2=R'_3=R'_5=R'_6=H$; $R'_4=CH_2$-CN (b) a heterocycle of formula

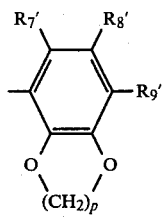

in which p, $R'_7$, $R'_8$ and $R'_9$ assume the following values:
- p=2; $R'_7=R'_8=H$; $R'_9$ represents the methoxy, acetoxy, methyl, cyano, acetyl, n-butyroyl, alkoxycarbonyl in which the alkyl is linear or branched and comprises 2 to 5 carbon atoms, cyclohexyloxy carbonyl, carboxamido, N-methyl carboxamido, N-cyclohexylcarboxamido, N-phenyl carboxamido, alkanoylamino whose linear or branched alkyl has 1 to 4 carbon atoms, cyclohexylcarbonylamino, benzoylamino, N-alkylcarbamoylamino whose linear or branched alkyl has from 1 to 5 carbon atoms, N-cyclohexylcarbamoylamino, N-phenylcarbamoylamino, N-(paramethoxyphenyl) carbamoylamino, N,N-dimethylcarbamoylamino, morpholino carbonylamino, N,N'-dimethyl carbamoylamino, or ethoxycarbonylamino or the hydroxymethyl, cyanomethyl, ethylacetate, carboxamidomethyl or N-methylcarboxamidomethyl chains.
- p=2; $R'_7=R'_9=H$; $R'_8$ represents the acetyl group.
- p=2; $R'_8=R'_9=H$; $R'_7$ represents the acetamido group.
- p=1 or 3; $R'_7=R'_8=H$; $R'_9$ represents the acetyl, acetamido or N-methylcarbamoylamino groups.

(c) a naphthalene nucleus of the type

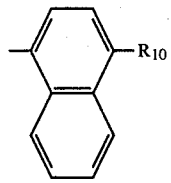

in which $R_{10}$ represents the acetyl, acetamido or N-methylcarbamoylamino groups.

(d) a heterocycle of the type

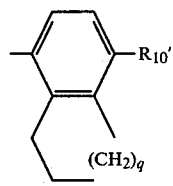

in which q and $R'_{10}$ assume simultaneously the following values:
- q=1 in which case $R'_{10}$ represents the acetamido and N-methyl-carbamoylamino groups
- q=2 in which case $R'_{10}$ represents the acetyl, acetamido or N-methylcarbamoylamino groups.

(e) the group

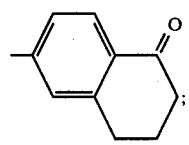

and
- X' represents a sulphur atom and the Ar' radical represents:

(f) an aromatic group

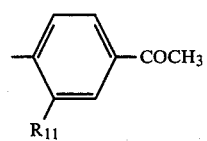

in which $R_{11}$ represents the hydrogen atom or the methoxy group.

(g) a heterocycle of the type

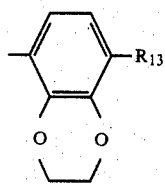

in which $R_{13}$ represents the hydrogen atom or the acetyl group.

The compounds of formula (III) result from the condensation of the phenols of formula (VII):

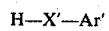

H—X'—Ar'     (VII)

in which X' and Ar' have the same meaning as in formula (III), with epichlorohydrin or epibromohydrin. This condensation is carried out preferably with reflux in acetone or acetonitrile in the presence of potassium carbonate.

The compounds of formula (VII) above are partially novel and are then prepared following different methods according to the nature of X' and Ar.

More exactly:

(1) The compounds of formula (VII) corresponding to formulae (VIIa), (VIIb), (VIIc):

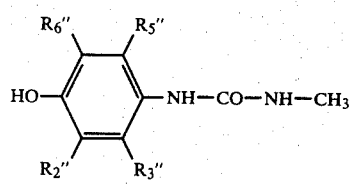

in which $R''_2$, $R''_3$, $R''_5$ and $R''_6$ assume simultaneously the following values:
- $R''_3 = R''_5 = R''_6 = H$; $R''_2 = CH_3$
- $R''_5 = R''_6 = H$; $R''_2 = R''_3 = OCH_3$
- $R''_3 = R''_5 = H$; $R''_2 = R''_6 = Cl$
- $R''_3 = R''_5 = H$; $R''_2 = R''_6 = OCH_3$

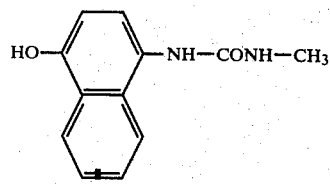

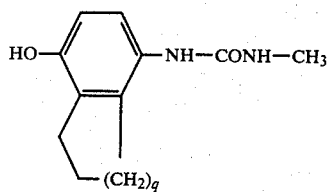

in which q assumes the values 1 or 2, are obtained by action of methyl isocyanate, in a chloroform solution, respectively on the amino phenols of formulae:

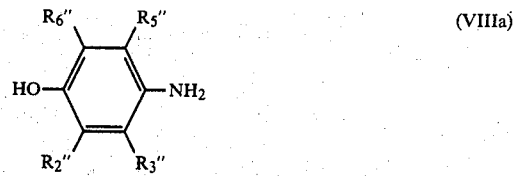

in which the values $R''_2$, $R''_3$, $R''_5$ and $R''_6$ have the same meanings as in (VIIa),

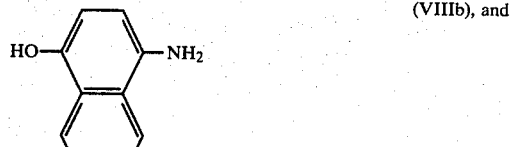

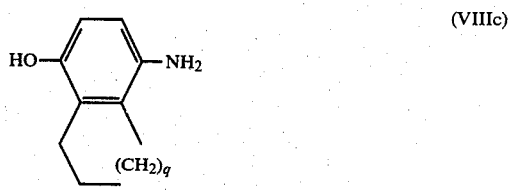

in which q assumes the values 1 or 2.

(2) The compounds (VII) corresponding to the formula (VIId):

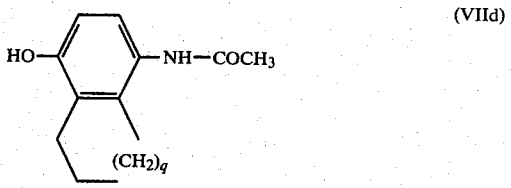

in which q assumes the values 1 or 2, are obtained by condensation of acetic anhydride on the (VIIIc) compounds in an aqueous solution.

(3) The compounds (VII) corresponding to formulae (VIIe) and (VIIf):

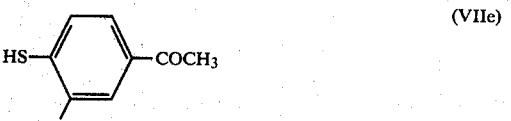

in which $R_{13}$ represents the hydrogen atom or the acetyl group are obtained by treatment with a solution of NaOH in methanol of compounds of formulae (IX) and (IXa)

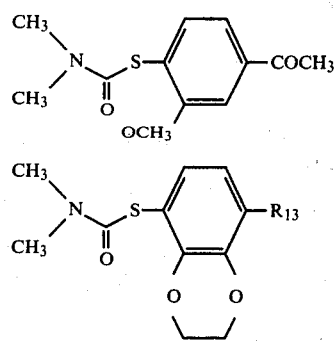
(IX)

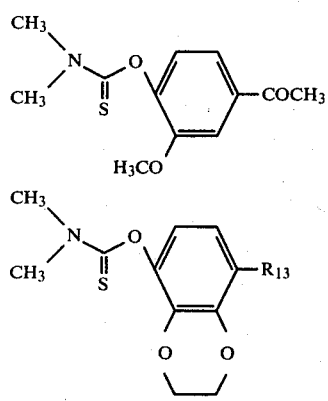
(IXa)

in which $R_{13}$ represents the hydrogen atom or the acetyl group.

The (IX) and (IXa) compounds are obtained by thermal transposition of compounds (X) and (Xa)

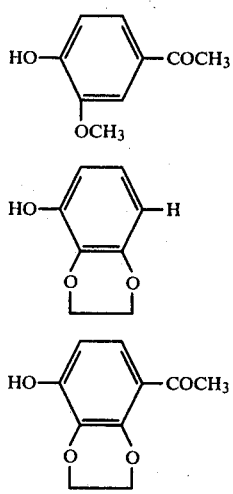
(X)

(Xa)

in which $R_{13}$ has the same meanings as in (IXa).

The (X) and (Xa) compounds are themselves obtained by condensation of N,N-dimethylthiocarbamoyl chloride with phenols of formulae:

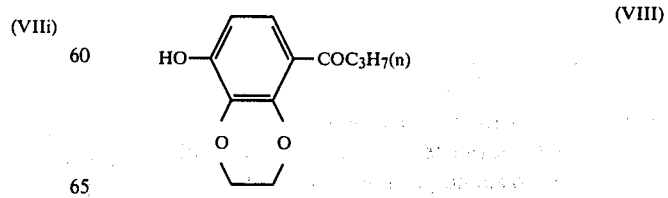
(VIIg)

(VIIh)

(VIIi)

(4) The compounds of formula (VII) corresponding to formula (VIIk)

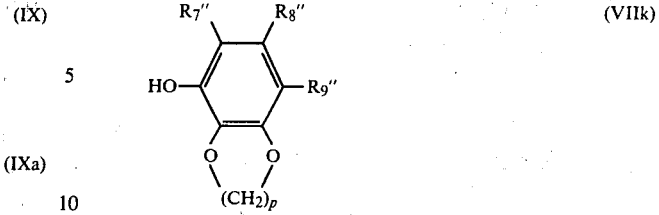
(VIIk)

in which p, $R''_7$, $R''_8$ and $R''_9$ assume simultaneously the following values:

- $p=2$; $R''_7 = R''_8 = H$; $R''_9$ represents the acetoxy, cyano, alkoxy carbonyl in which the alkyl is linear or branched and comprises 2 to 5 carbon atoms, cyclohexyloxy carbonyl, carboxamido, N-methyl carboxamido, N-cyclohexyl carboxamido, N-phenyl carboxamido, alkanoylamino whose alkyl is linear or branched and has 2 to 5 carbon atoms, cyclohexylcarbonylamino, benzoylamino, N-alkylcarbamoylamino whose alkyl is linear or branched and has 1 to 5 carbon atoms, N-cyclohexylcarbamoylamino, N-phenylcarbamoylamino, N-paramethoxyphenyl carbamoylamino, N,N-dimethyl carbamoylamino, morpholinocarbonylamino, N,N'-dimethyl-carbamoylamino, or ethoxycarbonylamino group; or the hydroxymethyl, cyanomethyl, ethyl acetate, carboxamidomethyl and N-methylcarboxamido methyl chains,
- $p=1$ or 3; $R''_7 = R''_8 = H$; $R''_9$ then represents the acetyl, acetamino or N-methylcarbamoylamino groups, are obtained by hydrogenolysis, in the presence of palladium on charcoal, of compounds of formula (XI)

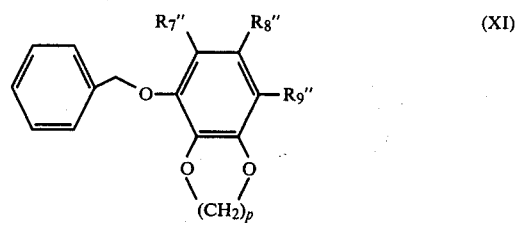
(XI)

in which p, $R''_7$, $R''_8$ and $R''_9$ have the same meanings as in (VIIk).

(5) The (VII) compound corresponding to the formula VIII)

(VIII)

HO—⬡—COC$_3$H$_7$(n)

is obtained by the transposition of Fries of the compound of formula (XII)

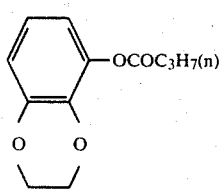
(XII)

(6) The (VII) compound corresponding to formula (VIIm)

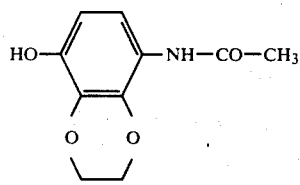
(VIIm)

is obtained by a Beckmann rearrangement, in an acetic acid medium, in the presence of a hydrochloric acid, of the compounds of formula (XIII)

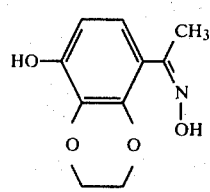
(XIII)

Compound (XIII) is itself obtained by action of hydroxylamine on the compound of formula (VIIi)

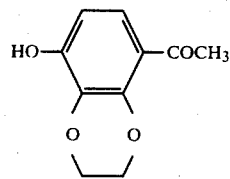
(VIIi)

(7) The compound of formula (VII) corresponding to formula (VIIn)

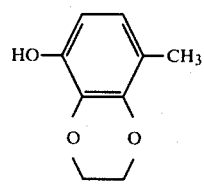
(VIIn)

is obtained by hydrogenolysis, in the presence of palladium on 5% charcoal, of the compound of formula (XIp) used in the crude state

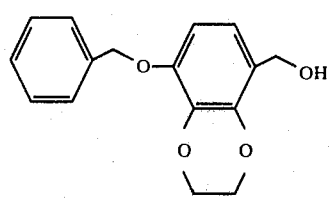
(XIp)

The compounds of formula (XI) above, necessary in the preparation of the compounds of formula (VIIk) are partly novel and are obtained by different processes depending on the nature of p, $R''_7$, $R''_8$ and $R''_9$.

Similarly, the compound of formula (XIa) is novel:

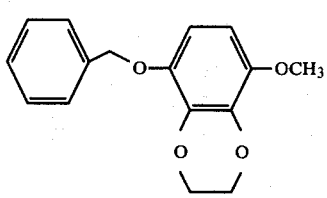
(XIa)

which can be used for the synthesis of a compound of formula (VIIk'), which is known:

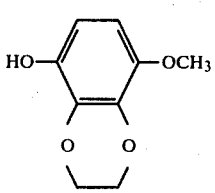
(VIIk')

More exactly:

(1) The compound corresponding to formula (XIa)

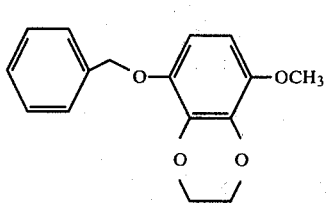
(XIa)

is obtained by action of methyl sulfate on the compound of formula (XIV)

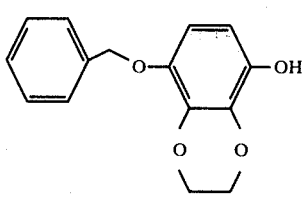
(XIV)

The compound (XIV) is obtained by action of potassium carbonate on the following compound (XIb)

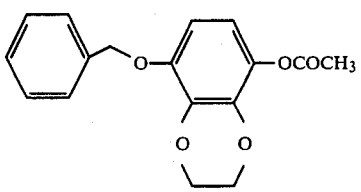
(XIb)

which is itself obtained by Baeyer Williger reaction on the compound of formula (XV)

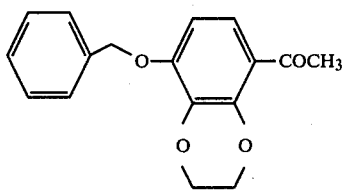
(XV)

The novel compound (XV) is obtained by action of benzyl chloride, in solution in acetonitrile or acetone, in the presence of potassium carbonate, on the compound (VIIi):

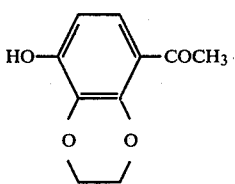
(VIIi)

(2) The compounds (XI) corresponding to the formula (XIc):

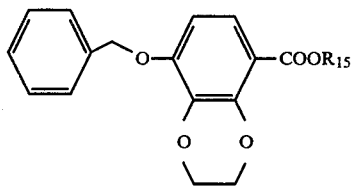
(XIc)

in which $R_{15}$ represents the ethyl, isopropyl, tert-butyl, n-pentyl, or cyclohexyl groups are obtained:

— when in (XIc) $R_{15}$ represents the isopropyl, t-butyl, n-pentyl, and cyclohexyl groups, by a synthesis in two stages which consists in treating the compound of formula (XVI)

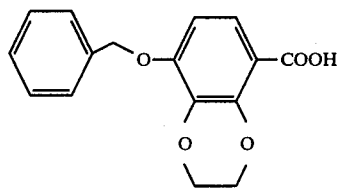
(XVI)

with thionyl chloride, then by reacting the crude product thus obtained with alcohols of formula (XVII):

$R_{15}$—OH (XVII)

in which $R_{15}$ has the same meaning as in formula (XIc), except for the ethyl group, and — when in (XIc) $R_{15}$ represents the ethyl group, by action of ethanol in the presence of hydrochloric acid, on the compound of formula (XVI).

The compound of formula (XVI), also novel, is obtained by oxidation by the iodine-pyridine complex, in the presence of soda, of the compound of formula (XV):

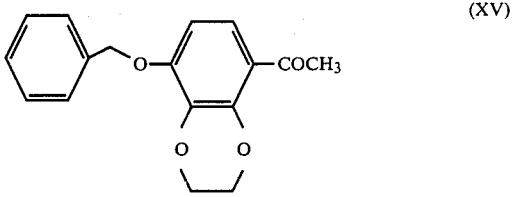
(XV)

(3) The (XI) compounds corresponding to the formula (XId):

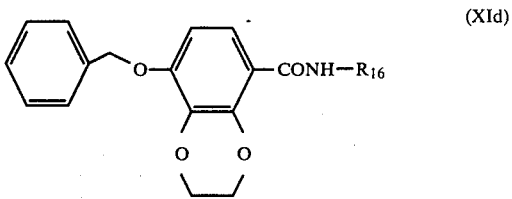
(XId)

in which $R_{16}$ represents either the hydrogen atom or the methyl, cyclohexyl or phenyl groups are obtained:

— when $R_{16}$ assumes the above meanings, except for the methyl group, by a two-stage synthesis which consists in treating the compound of formula (XVI) with thionyl chloride, then in reacting on the crude product thus obtained the amines of formula (XVIII)

$R_{16}$—$NH_2$ (XVIII)

in which $R_{16}$ represents the hydrogen atom or a cyclohexyl or phenyl group, and —when $R_{16}$ represents the methyl group, from the compound of formula (XVI) following the process of mixed anhydrides (with methylamine).

(4) The compounds (XI) corresponding to formula (XIe):

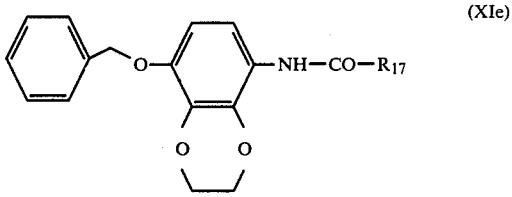
(XIe)

in which $R_{17}$ represents either a linear or branched alkyl group having from 2 to 5 carbon atoms, or the cyclohexyl group, or the phenyl group, are obtained by action of acid chlorides of formula (XIX):

$R_{17}COCL$ (XIX)

in which $R_{17}$ has the same meanings as in (XIe), on the compounds of formula (XX):

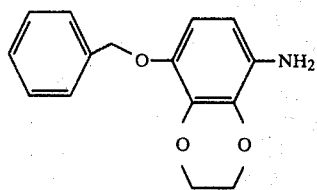
(XX)

in a tetrahydrofuran medium.

(5) The compounds of formula (XI) corresponding to formula (XIf):

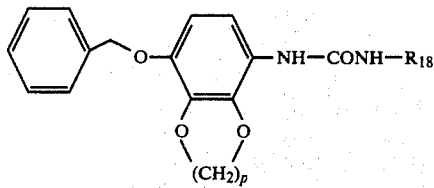
(XIf)

in which p and $R_{18}$ assume simultaneously the following values:
- p=2; $R_{18}$ represents either a linear or branched alkyl group having 1 to 5 carbon atoms or the cyclohexyl, phenyl or paramethoxyphenyl groups,
- p=1 or 3; $R_{18}$ represents the methyl group, are obtained by action of isocyanates of formula (XXI):

$R_{18}NCO$  (XXI)

on the compounds of formula (XX) above and (XXa)

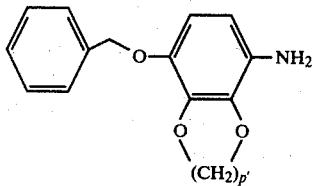
(XXa)

in which p′ assumes the values 1 or 3.

(6) The compound (XI) corresponding to formula (XIg):

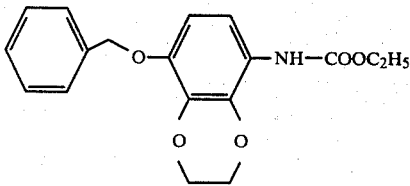
(XIg)

is obtained by action of ethyl chloroformate on the compound of formula (XX) above.

The compounds of formulae (XX) and (XXa) used in the synthesis given under items (4), (5) and (6) above are novel and are obtained by hydrolysis, with potash (KOH) in ethanol, of the compounds of formula (XIh)

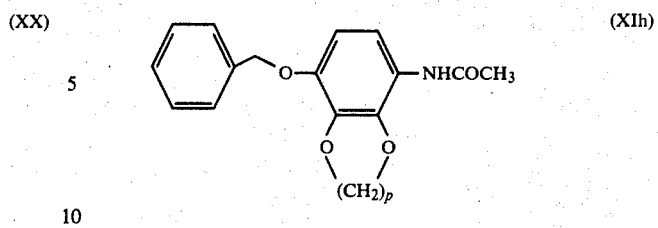
(XIh)

in which p assumes the values 1, 2 or 3.

The compounds of formula (XIh) are, for their part, obtained:

—either by a Beckmann rearrangement, in an acid medium, of the compounds of formula (XXII):

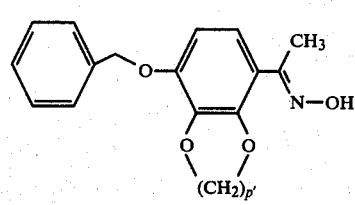
(XXII)

in which p′ assumes the values 1 or 3.

—or by action of benzyl chloride on the compound of formula (VIIm):

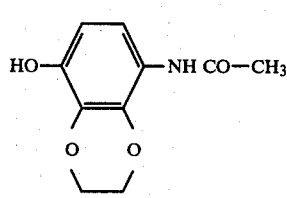
(VIIm)

in an acetone solution, in the presence of potassium carbonate.

The compounds of formula (XXII) above are obtained by action of hydroxylamine on the compounds of formula (XIi):

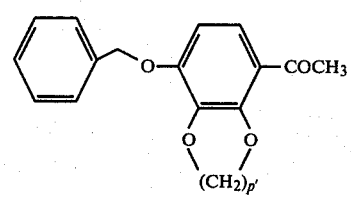
(XIi)

in which p′ assumes the values 1 or 3.

The compounds of formula (XIi) are obtained by action of a di-iodated or dibrominated derivative of formula (XXIII):

$I-(CH_2)_{p'}-I$ or $Br-(CH_2)_{p'}-Br$  (XXIII)

in which p′ assumes the value 1 or 3, on the compound of formula (XXIV):

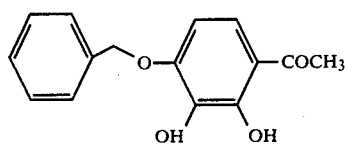

in solution in dimethyl sulfoxide or N,N-dimethylformamide in the presence of potash (KOH).

Compound (XXIV) is obtained by action of benzyl chloride on gallacetophenone.

(7) The compound (XI) corresponding to formula (XIj):

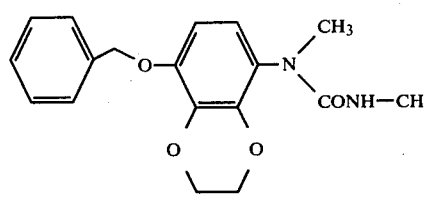

is obtained by action of methyl isocyanate on compound (XXV):

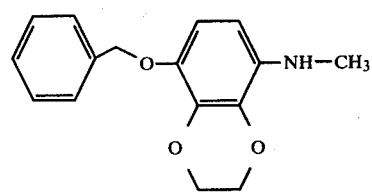

Compound (XXV) is obtained by a synthesis in two steps which consists in treating the compound of formula (XX) with a mixture of formaldehyde and dimethyl-5,5-hydantoin in an ethanol solution, then in reacting on the crude reaction product, sodium borohydride in solution in dimethylsulfoxide, at a temperature of 100° C.

(8) Compound (XI) corresponding to formula (XIk):

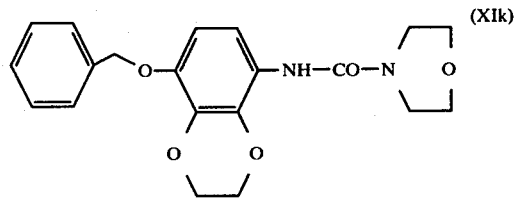

is obtained by action of morpholine at reflux on the compound of formula (XIg):

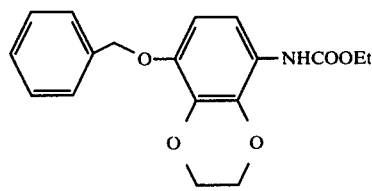

(9) Compound (XI) corresponding to formula (XII):

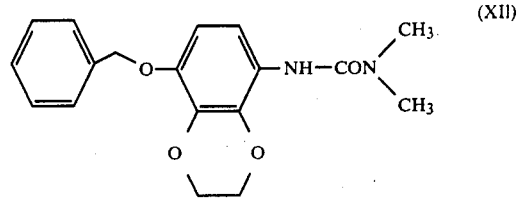

is obtained by action of N,N-dimethylcarbamoyl chloride on the compound of formula (XX).

(10) Compound (XI) corresponding to formula (XIm):

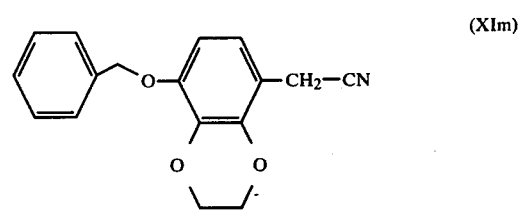

is obtained by action of sodium cyanide on the compound of formula (XXVI):

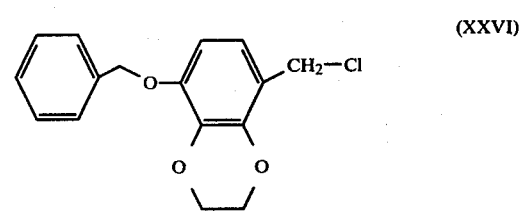

Compound (XXVI) is obtained by action of thionyl chloride on compound (XIp), hereafter described.

(11) Compound (XI) corresponding to formula (XIn):

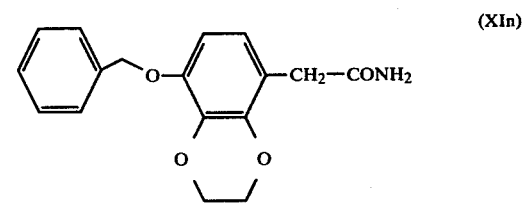

is obtained by treating compound (XIm):

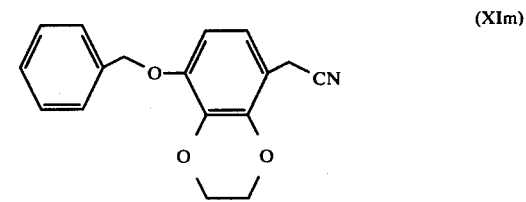

by potash KOH in solution in t-butanol.

(12) Compound (XI) corresponding to formula (XIo):

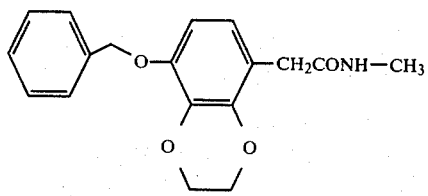
(XIo)

is obtained by action of methylamine following the mixed anhydride method on the compound of formula (XXVII):

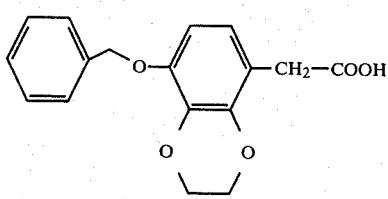
(XXVII)

Compound (XXVII) is obtained by saponification with an aqueous solution of NaOH of compound (XIm).

(13) Compound (XI) corresponding to formula (XIp):

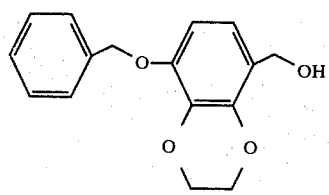
(XIp)

is obtained by reduction with the double hydride of lithium and aluminum of the compound of formula (XIc), in which $R_{15}$ represents the ethyl group.

(14) Compound (XI) corresponding to formula (XIq):

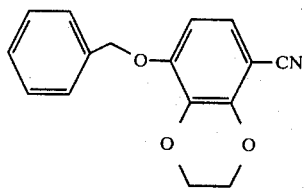
(XIq)

is obtained by action of phosphorous pentachloride on the compound (XId) in which $R_{16}$ represents the hydrogen atom.

(15) Compound (XI) corresponding to formula (XIr):

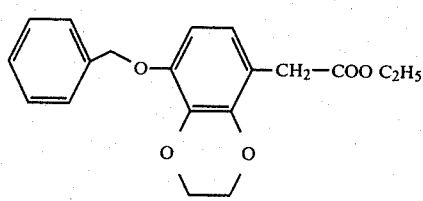
(XIr)

is obtained by action of ethanol, in the presence of hydrochloric acid, on the compound of formula (XXVII):

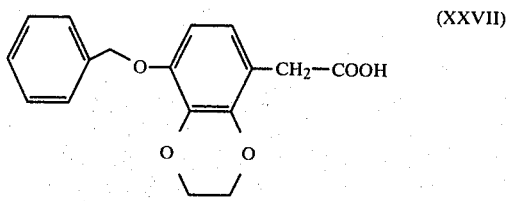
(XXVII)

The process for the preparation of the compounds of formula (I) in which:

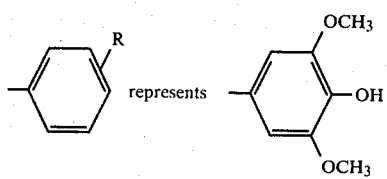

represents or else

—the radical Ar represents

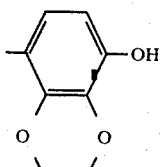

consists in hydrolyzing the acetoxy group of compounds of formulae (Ia) and (Ib)

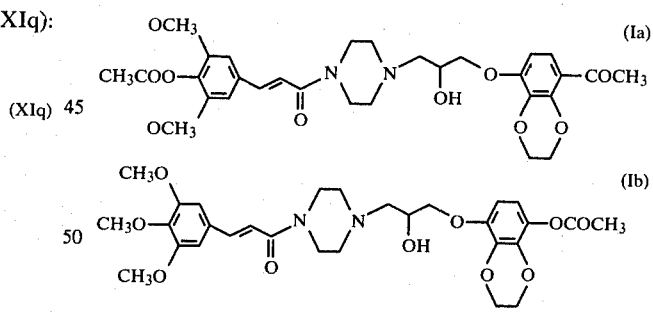
(Ia)

(Ib)

with an alcohol solution of sodium bicarbonate.

The compounds of formulae (Ia) and (Ib) are obtained by a process identical to that used for the synthesis of compounds of formula (I) previously described.

The process for the preparation of the compounds of formula (I) in which X represents the methylamino group:

consists in condensing an epoxy of formula (IIIh):

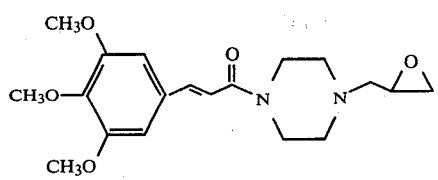
(IIIh)

with N-methylaniline in an alcohol medium.

The compound of formula (IIIh) is obtained by condensing epibromohydrin on 3,4,5-trimethoxy cinnamoylpiperazine of formula (IIc):

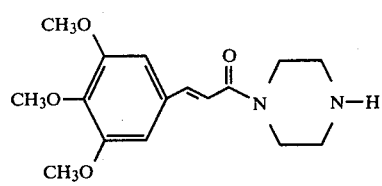
(IIc)

in solution in acetonitrile, in the presence of potassium carbonate.

The process for the preparation of compounds of formula (I), in which $R_1$ represents the hydrogen atom consists in condensing piperazine of formula (IIc) above with a chlorinated derivative of formula (XXVIII):

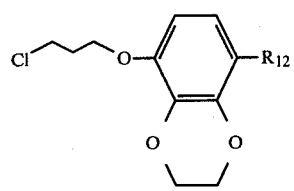
(XXVIII)

in which $R_{12}$ represents the acetyl, acetamido, N-methyl carboxamido or N-methylcarbamoyl amino groups in solution in acetonitrile, in the presence of potassium carbonate.

The novel compounds of formula (XXVIII) are obtained by condensation of 1-bromo-3-chloro-propane with the phenols of formula (VII):

H—X'—Ar' (VII)

in which X' represents the oxygen atom and Ar' is

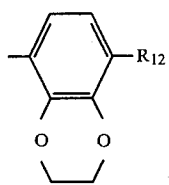

in which $R_{12}$ has the same meanings as in formula (XXVIII).

The following preparations are given by way of example to illustrate the invention.

EXAMPLE 1:
1-(4-cyano-2,3-ethylenedioxy-phenoxy)-2,3-epoxypropane (III) Code Number: 770584

A mixture of 31 g of 5-cyano-8-hydroxy-1,4-benzodioxane (VII) (Code number 770583), 38.35 g of epibromohydrin and 133 g of potassium carbonate in 300 ml of acetonitrile was brought to reflux for 12 hours. The mixture was filtered, the product then crystallized in the filtrate, it was filtered out and recrystallized in acetonitrile.

31.6 g of product were obtained.
Yield: 79%
Melting point: 167° C.
Empirical formula: $C_{12}H_{11}NO_4$
Molecular weight: 233.116
Elementary analysis:

|  | C | H | N |
|---|---|---|---|
| Calculated % | 61.82 | 4.76 | 6.01 |
| Obtained % | 61.92 | 4.76 | 5.95 |

By the same process, but from the corresponding reagents, the compounds of formula (III), appearing in Table I below, were obtained.

TABLE I

| Code Number | X' | —Ar' | Empirical Formula | Molecular Weight | Melting Point °C. | Yield % | IR or NMR spectrum or elementary analysis |
|---|---|---|---|---|---|---|---|
| 780 008 | oxygen | —⟨benzodioxane⟩—OCH₃ | $C_{12}H_{14}O_5$ | 238.232 | 110 | 83 | NMR (CDCl₃) ∂ ppm: 6.5, d (J = 10Hz); 6.35d(J = 10Hz) & 4.3s (6 benzodioxane protons) 3.8s OCH₃ 4.1, 3.35 + 2.7 5,m O⟨epoxide⟩ |
| 780 003 | " | —⟨benzodioxane⟩—OCOCH₃ | $C_{13}H_{14}O_6$ | 266.242 | 160 | 91 | Elementary analysis: C H Cal. (%) 58.64 5.30 Obt. (%) 58.60 5.43 |
| 770 584 | " | —⟨benzodioxane⟩—CN | $C_{12}H_{11}NO_4$ | 233.116 | 167 | 79 | Elementary analysis: C H N Cal. (%) 61.82 4.76 6.01 Obt. (%) 61.92 4.76 5.95 |

TABLE I-continued

| Code Number | X' | —Ar' | Empirical Formula | Molecular Weight | Melting Point °C. | Yield % | IR or NMR spectrum or elementary analysis |
|---|---|---|---|---|---|---|---|
| 780 372 | " | benzodioxane-COO-iPr | $C_{15}H_{18}O_6$ | 294.294 | | 65 | NMR (CDCl$_3$) δ ppm: 7.35,d (J = 10Hz); 6.5,d(J = 10Hz) & 4.35s (6 benzodioxane protons) 5.15,m;1.35,d(J = 6Hz) COO— 4.2;3.35 & 2.8 m O |
| 780 368 | " | benzodioxane-COO+ | $C_{16}H_{11}O_6$ | 305.296 | 57 | 87 | Elementary analysis:<br>    C    H<br>Cal. (%) 62.32  6.54<br>Obt. (%) 62.47  6.66 |
| 780 300 | " | benzodioxane-COOC$_5$H$_{11}n$ | $C_{17}H_{21}O_6$ | 321.338 | 83 | 77 | Elementary analysis:<br>    C    H<br>Cal. (%) 63.24  6.88<br>Obt. (%) 63.21  6.75 |
| 780 332 | " | benzodioxane-COO-cyclohexyl | $C_{18}H_{21}O_6$ | 333.348 | 79 | 64 | Elementary analysis:<br>    C    H<br>Cal. (%) 64.66  6.63<br>Obt. (%) 64.57  6.46 |
| 770 204 | " | benzodioxane-CONH$_2$ | $C_{12}H_{13}NO_5$ | 251.232 | 209 | 86.5 | NMR (DM SO) δ ppm:7.4,d(J = 10Hz); 6.7d(J = 10Hz) & 4.35s (6 benzodioxane protons) 7.3 m (CONH$_2$) 4.2; 3.2 & 2.7 m O |
| 760 708 | " | benzodioxane-CONHCH$_3$ | $C_{13}H_{15}NO_5$ | 265.258 | 132.5 | 89 | δ ppm: 7.42,d,(J = 10Hz); 6.51 d,(J = 10Hz) & 4.32,s, (6 benzodioxane protons) δ = 7.40(m) & 2.92,d,(J = 5Hz): CONH—CH$_3$ δ = 4.30; 3.35 & 2.80 m O |
| 770 830 | " | benzodioxane-CONH-cyclohexyl | $C_{18}H_{23}NO_5$ | 333.372 | 102 | 75 | NMR (DM SO)7.3,d(J = 10Hz); 6.65d(J = 10Hz) & 4.35s (6 benzodioxane protons) 7.6d; 1.0-2.0, (massive) CONH— 4.3; 3.35 & 2.7 m O |
| 770 851 | " | benzodioxane-CONH-phenyl | $C_{18}H_{17}NO_4$ | 327.324 | 190 | 87 | NMR δ ppm: 7.3,d(J = 10Hz); 6.7d(J = 10Hz) & 4.38s (6 benzodioxane protons) 7.8,m; 7.4,m; 11,s CONH— 4.3; 3.35 & 2.75 m O |
| 770 544 | " | benzodioxane-NHCO Et | $C_{14}H_{17}NO_5$ | 279.284 | 127 | 75 | NMR (CD Cl$_3$)δ ppm: 7.75,d(J = 10 Hz); 6.5d(J = 10Hz) & 4.28s (6 benzodioxane protons) 7.45,s; 2.35,q(J = 6Hz); 1.20,t(J = 6Hz) —NHCO$_2$Et 4.2;3.35&2.75m O |
| 770 600 | " | benzodioxane-NHCOC$_4$H$_9$ (n) | $C_{16}H_{21}NO_5$ | 307.336 | 121 | 79 | NMR (CD Cl$_3$)δ ppm: 7,8,d(J = 10 Hz) & 4.28s (6 benzodioxane protons) 7.5s; 2.4,m; 0.8 & 2.0 (massive) NHCOC$_4$H$_9$ (n) 4.2; 3.4 & 2.8m O |

TABLE I-continued

| Code Number | X' | —Ar' | Empirical Formula | Molecular Weight | Melting Point °C. | Yield % | IR or NMR spectrum or elementary analysis |
|---|---|---|---|---|---|---|---|
| 770 691 | " | benzodioxane-NHCO-iPr | $C_{15}H_{19}NO_5$ | 293.310 | 150 | 85 | NMR (CDCl$_3$) δ ppm: 7.82,d(J = 10 Hz); 6.53d(J = 10Hz) & 4.30s (6 benzodioxane protons) 2.4,m; 1.20,d (J = 6Hz); 7.5s NH CO—iPr 4.25; 3.35 & 2.8m O—CH(Et)(O) |
| 770 613 | " | benzodioxane-NHCO-tBu | $C_{16}H_{21}NO_5$ | 307.336 | 87 | 98 | NMR (CDCl$_3$) δ ppm: 7.8,d(J = 10 Hz); 6.45,d(J = 10Hz)& 4.25,s (6 benzodioxane protons) 7.8,s, 1.25,s NHCO+ 4.3; 3.35 & 2.80m O |
| 770 532 | " | benzodioxane-NHCO-cyclohexyl | $C_{18}H_{25}NO_5$ | 333.37 | 143 | 100 | NMR (CDCl$_3$)δ ppm: 7.8,d(J = 10 Hz); 6.5,d(J = 10Hz) & 4.35,s (6 benzodioxane protons) 7.5,s & 1.0 & 2.3 (massive) NHCO—cyclohexyl 4.3; 3.35 & 2.80 m O |
| 770 528 | " | benzodioxane-NHCO-Ph | $C_{18}H_{17}NO_5$ | 372.324 | 153 | 90 | NMR (CDCl$_3$) δ ppm: 7.9,d(J = 10Hz) 6.55,d(J = 10Hz) & 4.3 (6 benzodioxane protons) 8.2,s; 7.8s, 7.45,m NHCO—Ph 4.1; 3.35 & 2.8 m O |
| 770 306 | " | benzodioxane-NHCONH—Et | $C_{14}H_{18}N_2O_5$ | 294.300 | 196 | 90 | NMR (DMSO) δ ppm: 7.5,d(J = 10Hz) & 4.3,s (6 benzodioxane protons) 7.6,s;6.6,m;3.85,q(J = 6Hz) & 1.05,t(J = 6Hz) (NH—CONH—C$_2$H$_5$) 4.2; 3.3 & 2.8 m O |
| 770 482 | " | benzodioxane-NHCONHC$_3$H$_7$ (n) | $C_{15}H_{20}N_2O_5$ | 308.326 | 176 | 68 | NMR (DMSO) δ ppm: 7.45,d(J = 10Hz); 6.45,d(J = 10Hz) & 4.4,s (6 benzodioxane protons) 7.65s; 6.7,m; 3.9,m; 1.4,m & 0.9,d(J = 6Hz) (NHCONHC$_3$H$_7$n) 4.2; 3.1 & 2.8 m O |
| 770 629 | " | benzodioxane-NHCONH-iPr | $C_{15}H_{20}N_2O_5$ | 308.326 | 155 | 85 | NMR(DMSO δ ppm: 7.45,d(J = 10Hz); 6.45,d(J = 10Hz) & 4.3(6 benzodioxane protons)7.5,s; 6.65, s;3.75,m;1.1,d(J = 6Hz) (NHCONH—iPr) 4.2; 3.1 & 2.7m O |
| 770 633 | " | benzodioxane-NHCONHC$_4$H$_9$ (n) | $C_{16}H_{22}N_2O_5$ | 322.362 | 186 | 69 | NMR (DMSO) δ ppm: 7.5,d(J = 10Hz); 6.5,d(J = 10Hz) & 4.3s(6 benzodioxane protons) 7.6 5,s; 6.7,m;3.3m;3.1m;1.2,m & 0.95,m (NHCONHC$_4$H$_9$n) 4.24;3.3 & 2.8 m O |
| 770 710 | " | benzodioxane-NH—CONH-tBu | $C_{16}H_{22}N_2O_5$ | 322.352 | 146 | 28 | NMR(CDCl$_3$)δppm:7.3d(J = 10Hz); 6.4d(J = 10Hz)&4.1 (6 benzodioxane protons) 6.6,s; 5.1,s & 1.15s NHCONH+ 4.0; 3.3 & 2.7 m |
| 780 222 | " | benzodioxane-NHCONH-C$_6$H$_4$-OCH$_3$ | $C_{19}H_{20}N_2O_6$ | 372.366 | 220 | 85 | Elementary analysis: C H N Cal. (%) 61.28 5.41 7.52 Obt. (%) 61.00 5.45 7.62 |

TABLE I-continued

| Code Number | X' | —Ar' | Empirical Formula | Molecular Weight | Melting Point °C. | Yield % | IR or NMR spectrum or elementary analysis |
|---|---|---|---|---|---|---|---|
| 771 232 | " | benzodioxane-NHCON(CH$_3$)$_2$ | C$_{14}$H$_{18}$N$_2$O$_5$ | 294.300 | 160 | 80 | Elementary analysis:<br>　　　　C　　H　　N<br>Cal. (%) 57.13　6.17　9.52<br>Obt. (%) 56.82　6.25　9.24 |
| 771 148 | " | benzodioxane-NHCON(morpholine) | C$_{16}$H$_{20}$N$_2$O$_6$ | 336.336 | 164 | 55 | Elementary analysis:<br>　　　　C　　H　　N<br>Cal. (%) 57.13　5.99　8.33<br>Obt. (%) 56.98　6.10　8.33 |
| 771 237 | " | benzodioxane-N(CH$_3$)CONHCH$_3$ | C$_{14}$H$_{18}$N$_2$O$_5$ | 294.300 | oil | 88 | NMR(CD Cl$_3$)ppm(δ):6.75,d (J = 10Hz);6.5,d(J = 10Hz)&4.3,s (6 benzodioxane protons) 7.35, s;3.1,s & 2.7,d(J = 5Hz)<br>(N$<$CH$_3$ / CO NH CH$_3$) 4.3;3.3 & 2.8, m  O$\frown$O |
| 770 524 | " | benzodioxane-NHCOOEt | C$_{14}$H$_{17}$NO$_6$ | 295.284 | 130 | 95 | NMR(CDCl$_3$)ppm(δ):7.5,d(J = 10 Hz); 6.5,d(J = 10Hz)&4.25,s (6 benzodioxane protons) 6.8, s;4.2,q(J = 6Hz)&1.15,t(J = 6Hz) (NH CO$_2$Et) 4.15;3.35 & 2.75, m  O$\frown$O |
| 770 311 | " | benzodioxane-CH$_2$COOEt | C$_{15}$H$_{18}$O$_6$ | 294.294 | 72 | 85 | Elementary analysis:<br>　　　　C　　H<br>Cal. (%) 61.21　6.17<br>Obt. (%) 61.25　6.31 |
| 770 385 | " | benzodioxane-CH$_2$CONH$_2$ | C$_{13}$H$_{15}$NO$_5$ | 265.258 | 200 | 60 | NMR (DMSO)ppm(δ):6.7,d(J = 10 Hz);6.5,d(J = 10Hz)& 4.2,s (6 benzodioxane protons) 7.1,m; 3.3,s CH$_2$CONH$_2$ 4.2; 3.35 & 2.7,m |
| 770 381 | " | benzodioxane-CH$_2$CONHCH$_3$ | C$_{14}$H$_{17}$NO$_5$ | 269.284 | 174.6 | 75 | NMR(DMSO)ppm(δ): 6.65,d(J = 10 Hz);6.5(J = 10Hz)&4.2,s (6 benzodioxane protons) 7.5,m; 3.3,s;2.55,(J = 5Hz) (CH$_2$CONH—CH$_3$) 4.3;3.4 & 2.8,m |
| 780 307 | " | benzodioxole-COCH$_3$ | C$_{12}$H$_{12}$O$_5$ | 236.216 | 80 | 85 | Elementary analysis:<br>　　　　C　　H<br>Cal.(%) 61.01　5.12<br>Obt.(%) 60.80　4.81 |
| 780 345 | " | benzodioxole-NHCOCH$_3$ | C$_{12}$H$_{13}$NO$_5$ | 251.232 | 121 | 95 | NMR(CDCl$_3$)ppm(δ):7.3,d(10Hz); 6.5,d(10Hz)& 5.95,s (4 benzodioxole protons) 7.3,s; 2.15,s (NHCOCH$_3$) 4.4; 3.3 & 2.8,m |
| 780 408 | " | benzodioxole-NHCONHCH$_3$ | C$_{12}$H$_{14}$N$_2$O$_5$ | 266.248 | 168 | 75 | NMR(DMSO)ppm(δ):7.3;d(J = 10Hz) 6.5,d(J = 10Hz)&6.0,s (4 benzodioxole protons) 7.9,s; 6.2, m & 2.65,d(NH CO NH CH$_3$) 4.2; 3.35 & 2.8,m |
| 780 240 | " | benzodioxepine-COCH$_3$ | C$_{14}$H$_{15}$O$_5$ | 263.260 | 72 | 96 | NMR(CDCl$_3$)ppm(δ):7.4d(J = 10 Hz);6.65,d(J = 10Hz);4.3,m & 2.3,m(8 benzodioxepine protons) 2.53,s CO CH$_3$ 4.2; 3.4 & 2.8,m |

TABLE I-continued

| Code Number | X' | −Ar' | Empirical Formula | Molecular Weight | Melting Point °C. | Yield % | IR or NMR spectrum or elementary analysis |
|---|---|---|---|---|---|---|---|
| 780 392 | " | benzodioxepine-NHCOCH₃ | $C_{14}H_{17}O_5$ | 265.276 | 124 | 91 | NMR(CDCl₃)ppm(δ):7.85,d (J= 10 Hz); 6.65³,d (J= 10Hz); 4.25,m & 2.25,m (8 benzodioxepine protons) 7.75,s; 2.18,s NHCOCH₃ 4.2; 3.35 and 2.75,m |
| 780 467 | " | benzodioxepine-NHCONHCH₃ | $C_{14}H_{18}N_2O_5$ | 294.290 | 178 | 68 | NMR(DMSO)ppm(δ):7.65,d(J= 10Hz); 6.58,d (J=10Hz); 4.08, m & 2.1,m (8 benzodioxepine protons) 7.8,s; 6.6,m; 2.6,d NH CO NH CH₃ 4.1; 3.3 & 2.75,m |
| 760 845 | " | benzodioxane-CH₃ | $C_{12}H_{14}O_4$ | 222.232 | 66 | 92 | ppm (δ) = 6.63,d(J=10Hz); 6.42,d(J=10Hz);& 4.24,s: benzodio- xane protons = 2.16,s: —CH₃ = 4.21; 3.18 & 2.80, m |
| 740 454 | " | benzodioxane-COCH₃ | $C_{13}H_{14}O_5$ | 250.24 | 128 |  | Elementary analysis:<br>   C    H<br>Cal. (%) 62.39  5.63<br>Obt. (%) 62.15  5.79 |
| 760 698 | " | benzodioxane-COOEt | $C_{14}H_{16}O_6$ | 280.268 | 95 | 100 | ppm (δ) 7.42 & 6.51,d (J=10 Hz; 4.32,s: benzo- dioxane protons =4.30,q (J=7Hz)&1.35, t (J=7Hz):COOEt =428; 3.38; 2.80,m: |
| 750 568 | " | benzodioxane-NHCOCH₃ | $C_{13}H_{15}NO_5$ | 265.26 | 180 |  | Elementary analysis:<br>   C    H    N<br>Cal. (%) 58.86  5.70  5.70  5.28<br>Obt.(%) 58.62  5.13  5.13 |
| 770 609 | " | benzodioxane-NHCOC₃H₇ (n) | $C_{15}H_{19}NO_5$ | 293.310 | 133 | 76 | NMR(CDCl₃)ppm(δ): 7.78d, (J= 10Hz);6.5,d(J=10Hz)&4.28,s (benzodioxane protons) 7.4,s, 2.3,m; 1.7,m & 0.97,t (NH CO— C₃H₇n) 4.1; 3.35 & 2.80,m |
| 770 080 | " | benzodioxane-NHCONH-cyclohexyl | $C_{18}H_{24}N_2O_5$ | 348.388 | 220 | 70 | ppm(δ) = 7.50&6.45,d(J=10Hz); 4.23,s:benzodioxane protons =7.45&6.70,m—NH—CO—NH— =1.5,m: =4.20;3.60;2.64;m: |
| 770 084 | " | benzodioxane-NHCONH—φ | $C_{18}H_{18}N_2O_5$ | 342.34 | 208 | 75 | ppm(δ) = 7.60&6.55,d(J=10Hz); 4.32,s:benzodioxane protons = 8.10&6.70,m:—NH—CONH— = 7.30,m: = 4.20;3.40;&2.72,m |
| 770 076 | " | benzodioxane-NHCONHCH₃ | $C_{13}H_{16}N_2O_5$ | 280.274 | 235 | 40 | ppm(δ) = 7.50&6.51,d(J=10Hz); 4.30,s:benzodioxane protons = 7.68,s&6.55,m: —NH—CO—NH— = 2.62,d(J=5Hz); —CH₃ = 4.02,3.32;&2.70,m |

TABLE I-continued

| Code Number | X' | —Ar' | Empirical Formula | Molecular Weight | Melting Point °C. | Yield % | IR or NMR spectrum or elementary analysis |
|---|---|---|---|---|---|---|---|
| 760 703 | " | benzodioxane-CH₂OH | $C_{12}H_{14}O_5$ | 238.38 | oil | 93 | Elementary analysis:<br>　　　　C　　H<br>Cal. (%)　60.50　5.92<br>Obt. (%)　60.78　5.82 |
| 770 186 | " | benzodioxane-CH₂CN | $C_{13}H_{13}NO_4$ | 247.242 | 138 | 86 | ppm(δ) = 6.85;&6.52;d(J=10Hz) &4.32,s:benzodioxane protons<br>= 3.60,s:—CH₂—CN<br>= 4.18; 3.22 & 2.90,m $O\diagdown\diagup O$ |
| 780 388 | S | benzodioxane | $C_{11}H_{12}O_3S$ | 224.272 | oil | 85 | Elementary analysis:<br>　　　　C　　H<br>Cal. (%)　58.91　5.39<br>Obt. (%)　58.50　5.20 |
| 780 383 | S | benzodioxane-COCH₃ | $C_{13}H_{14}O_4S$ | 266.308 | 72 | 97 | Elementary analysis:<br>　　　　C　　H<br>Cal. (%)　58.63　5.30<br>Obt. (%)　58.77　5.53 |

EXAMPLE 2: 2-methoxy-4-acetyl thiophenol (VIIe)
Code Number: 780 472

—1st step:
1-N,N-dimethylthiocarbamoyloxy-2-methoxy-4-acetyl-benzene (X) Code Number: 780 470

A solution of 3.3 g of acetovanillone, of 2.9 g of dimethyl thiocarbamoyl and of 8.2 g of potassium carbonate in 80 cm³ of acetonitrile was brought to 70° C. for 30 minutes. After filtering, the solvent was evaporated and the residue recrystallized in ethanol. 3.3 g of product were obtained.
Yield: 66%
Melting point: 130° C.

NMR spectrum δ ppm = 7.54, m & 7.11, d, (J = 9Hz): aromatic protons
= 3.82, s —OCH₃
= 3.21, s, and 3.15, s,: —N(CH₃)(CH₃) 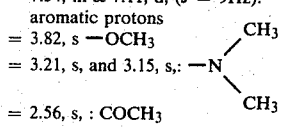
= 2.56, s, : COCH₃

By the same process, but from the corresponding reagents, the following compounds of formula (Xa) were obtained:

5-N,N-dimethylthiocarbamoyloxy-1,4-benzodioxane
Code Number: 780 385
Yield: 98%
Melting point: 98° C.
Empirical form.: $C_{11}H_{13}NO_3S$
Molecular weight: 239.39
Elementary analysis:

|  | C | H | N |
|---|---|---|---|
| Calculated (%) | 55.21 | 5.48 | 5.85 |
| Obtained (%) | 55.10 | 5.40 | 5.62 |

5-N,N-dimethylthiocarbamoyloxy-8-acetyl-1,4-benzodioxane
Code Number: 780 380

Yield: 75%
Melting point: 149° C.
Empirical formula: $C_{13}H_{15}NO_4S$
Molecular weight: 281.32
Elementary analysis:

|  | C | H | N |
|---|---|---|---|
| Calculated (%) | 55.50 | 5.37 | 4.98 |
| Obtained (%) | 55.34 | 5.21 | 4.68 |

—2nd step:
1-N,N-dimethylcarbamoylthio-2-methoxy-4-acetylbenzene (IX) Code Number: 780 471

Under a flow of argon, 13 g of 1-N,N-dimethylthiocarbamoyloxy-3-methoxy-4-acetylbenzene, obtained in the preceding step were heated for 35 minutes at 250° C. Then, the residue was chromatographed on a silica column. After elution with chloroform 6 g of product were obtained:
Yield: 46%
Melting point: 116° C.

NMR spectrum δ ppm = 7.57, s, aromatic protons
= 3.91, s, : —OMe
= 3.03, s, : —N(CH₃)(CH₃) 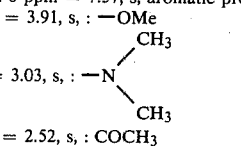
= 2.52, s, : COCH₃

By the same process, but from the corresponding reagents, the following compounds of formula (IXa) were obtained:

5-N,N-dimethylcarbamoylthio-1,4-benzodioxane
Code Number: 780 386
Yield: 59%
Melting point: 78° C.

NMR spectrum: δ ppm = 6.98, m; and 4.22, s: benzodioxan protons

= 3.02, s, —N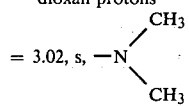

IR spectrum: band at 1640 cm⁻¹

—S—CO—N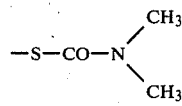

5-N,N-dimethylcarbamoylthio-8-acetyl-1,4-benzodioxane
Code Number: 780 381
Yield: 39%
Melting point: 155° C.
Empirical formula: C$_{13}$H$_{15}$NO$_4$S
Molecular weight: 281.32
Elementary analysis:

|  | C | H | N |
|---|---|---|---|
| Calculated (%) | 55.50 | 5.37 | 4.98 |
| Obtained (%) | 55.73 | 5.54 | 5.05 |

— 3rd step: 2-methoxy-4-acetylthiophenol (VIIe) Code Number: 780 472

A solution of 5.6 g of 4-N,N-dimethylthiocarbamoyloxy-3-methoxy acetophenone obtained in the previous step, 2.6 g of soda (NaOH) in 210 ml of methanol and 60 ml of water was brought to reflux for two hours. Then, the solvents were evaporated, the residue was taken up in water, washed with ethyl acetate, the aqueous phase was acidified with concentrated hydrochloric acid, extracted with chloroform which was dried and the solvent was evaporated. 3.5 g of product were obtained.
Yield: 87%
Melting point: 50° C.

| NMR spectrum: δ ppm | = 7.20, m: aromatic protons |
|---|---|
|  | = 4.16, s: -SH |
|  | = 3.96, s, : -OMe |
|  | = 2.57, s, : -COCH$_3$ |

By the same process, but from the corresponding reagents, the compounds of formula (VIIf), code numbers 780 387 and 780 382, shown in Table II below, were obtained.

EXAMPLE 3: 5-hydroxy-8-N-cyclohexyl carboxamido-1,4-benzodioxane (VIIk) Code Number: 770 829

A solution of 34.5 g of 5-benzyloxy-8-N-cyclohexyl-carboxamido-1,4-benzodioxane (XIId), code number 770 828, in presence of 6.8 g of palladium on 5% charcoal was hydrogenolysed in an autoclave at room pressure and temperature. Once the absorption of hydrogen was completed, and after filtration, the filtrate was evaporated.
Yield: 92%
Melting point: 182° C.

NMR spectrum: δ ppm = 7.24, d; 6.48, d, (J = 10Hz) and 4.18 s, : benzodioxane protons
= 7.62, d, (J = 7Hz): —CONH—
= 10.1, m, : —OH = 3.78, m and 1.5, m,: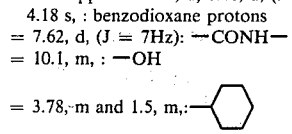

By the same process, but from the corresponding reagents, the compounds of formula (VII), corresponding to formula (VIIk) shown in Table II below, were obtained.

EXAMPLE 4:
5-hydroxy-8-n-propylcarbonyl-1,4-benzodioxane (VIII)
Code Number: 750 769

A solution of 44.4 g (0.2 mole) of 8-n-propylcarbonyl oxy-1,4-benzodioxane in 240 ml of nitrobenzene was cooled to a temperature of less than 10° C. and 40 g (0.3 mole) of aluminum chloride were slowly added. It was left for 48 hours at room temperature, diluted with water, the organic phase was decanted, the solvent was evaporated, and the residue was chromatographed on a silica column. With toluene-chloroform mixtures, 27 g (61%) of 5-hydroxy-6-n-propylcarbonyl-1,4-benzodioxane were eluted. Then, with a 90% chloroform-10% methanol mixture, 5 g of 5-hydroxy-8-n-propylcarbonyl-1,4-benzodioxane-1,4 were eluted.
Yield: 11%
Melting point: 84° C.
Empirical formula: C$_{12}$H$_{14}$O$_4$
Molecular weight: 222.23
Elementary analysis:

|  | C | H |
|---|---|---|
| Calculated (%) | 64.87 | 6.35 |
| Obtained (%) | 64.84 | 6.24 |

EXAMPLE 5:
5-hydroxy-8-acetamido-1,4-benzodioxane (VIIm) Code number: 750 548

— 1st step: 5-hydroxy 8-acetyl-1,4-benzodioxane oxime (XIII) Code number: 750 527

A solution of 19.4 g (0.1 mole) of 5-hydroxyl 8-acetyl-1,4-benzodioxane (VIIi) and 10.4 g (0.15 mole) of hydroxylamine hydrochloride in 50 ml of pyridine and 50 ml of ethanol was brought to reflux for 7 hours. Then, the solvents were evaporated and the residue crystallized in water. 12 g of product were obtained.
Yield: 55%
Melting point: 145° C.
Empirical form.: C$_{10}$H$_{11}$NO$_4$½H$_2$O
Molecular weight: 218.20
Elementary analysis:

|  | C | H | N |
|---|---|---|---|
| Calculated (%) | 55.04 | 5.54 | 6.42 |
| Obtained (%) | 55.24 | 5.68 | 6.31 |

— 2nd step: 5-hydroxy-8-acetamido-1,4-benzodioxane 250 ml of acetic acid were saturated with gaseous hydrochloric acid, then 20.9 g (0.1 mole) of 5-hydroxy- 8-acetyl-1,4-benzodioxane oxime, obtained in the previous step, were added. It was brought to reflux for 5 hours, then the solvents were evaporated, the residue was crystallized in water and recrystallized in ethanol. 7 g of product were obtained.

Yield: 33%
Melting point: 170° C.
Empirical formula: $C_{10}H_{11}NO_4$
Molecular weight: 209.20
Elementary analysis:

|  | C | H | N |
|---|---|---|---|
| Calculated (%) | 57.41 | 5.30 | 6.70 |
| Obtained (%) | 57.17 | 5.31 | 6.54 |

EXAMPLE 6: 5-hydroxy-8-methyl-1,4-benzodioxane (VIIn) Code number: 760 844

A solution of 14.7 g (0.05 mole) of 5-benzyloxy-8-hydroxymethyl-1,4-benzodioxane (XIp) code number 760 701, crude, non-crystallized, in 300 ml of absolute alcohol was hydrogenolysed at room pressure and temperature, in the presence of 3 g of palladium on 5% charcoal. Once the absorption of hydrogen was completed, the catalyst was filtered and the solvent was evaporated. A liquid was obtained.

NMR spectrum:

| $\delta$ ppm | = 8.90, s, 1 phenolic proton |
|---|---|
|  | = 6.42 and 6.21, d, (J=10Hz) |
|  | = 4.17, s,: benzodioxane protons |
|  | = 1.98, s,: —$CH_3$ |

EXAMPLE 7:
5-benzyloxy-8-methoxy-1,4-benzodioxane (XIa) Code number: 780 006

—1st step: 5 benzyloxy-8-acetyl-1,4-benzodioxane (XV) Code Number: 760 694

A suspension of 97 g (0.5 mole) of 5 hydroxy-8-acetyl-1,4-benzodioxane (VIIi), of 127 g (1 mole) of benzyl chloride and 155 g (1.12 mole) of potassium carbonate in 150 ml of absolute alcohol was brought to reflux for 24 hours. After filtration the solvent was evaporated, the residue was taken up in chloroform, washed with a solution of soda (NaOH) 1 N, the solvent was evaporated and the product was crystallized in alcohol, 135 g of product expected were obtained.

Yield: 95%
Melting point: 133° C.
Empirical formula: $C_{17}H_{16}O_4$
Molecular weight: 284.29
Elementary analysis:

|  | C | H |
|---|---|---|
| Calculated (%) | 71.82 | 5.67 |
| Obtained (%) | 71.76 | 5.76 |

—2nd step: 5-benzyloxy-8-acetoxy-1,4-benzodioxane (XIb) Code Number: 780 001

To a solution of 58 g of 5-benzyloxy-8-acetyl-1,4-benzodioxane (XV) obtained in the previous step, in 300 ml of formic acid, were added, at $-5°$ C., 25 g of a 36% solution of hydrogen peroxide in 100 ml of formic acid.

The mixture was left at 0° C. for 72 hours then poured on a mixture of water and ice, the precipitate formed was filtered, washed in water and recrystallized in a mixture of ethyl acetate and isopropyl ether.

Yield: 89%
Melting point: 104° C.
Empirical formula: $C_{17}H_{16}O_5$
Molecular weight: 300.39
Elementary analysis:

|  | C | H |
|---|---|---|
| Calculated (%) | 67.97 | 5.37 |
| Obtained (%) | 68.15 | 5.55 |

—3rd step: 5-benzyloxy-8-hydroxy-1,4-benzodioxane (XIV) Code Number: 780 005

To a solution of 58.3 g of 5-benzyloxy-8-acetoxy-1,4-benzodioxane obtained in the previous step, in 400 ml of methanol, are added 75 g of potassium carbonate, at room temperature. Then, after 30 minutes, the solution was filtered, the solvent evaporated, and the residue was taken up in water and acidified in concentrated hydrochloric acid. The precipitate obtained was filtered and recrystallized in alcohol: 47.3 g of the product were obtained.

Yield: 94%
Melting point: 131° C.
Empirical formula: $C_{15}H_{14}O_4$
Molecular weight: 258.25
Elementary analysis:

|  | C | H |
|---|---|---|
| Calculated (%) | 69.75 | 5.46 |
| Obtained (%) | 69.83 | 5.39 |

—4th step: 5-benzyloxy-8-methoxy-1,4-benzodioxane (XIa) Code Number: 780 006

To a solution of 45 g of 5-benzyloxy-8-hydroxy-1,4-benzodioxane obtained in the preceding step and 52 g of potassium carbonate in 500 ml of acetone, there was slowly added 33.5 g of dimethylsulfate then 20 ml of a 10% solution of methanolic caustic potash. The solution was then brought to reflux for 2 hours and 30 minutes, filtered, the solvents were evaporated, the residue was taken up in ethyl ether, washed with water, dried and the solvent was evaporated. 47 g of product were obtained.

Yield: 98%
Melting point: 70° C.
NMR Spectrum:

| $\delta$ ppm | = 7.36, d, and 6.47, d, (J=2Hz) and |
|---|---|
|  | 4.23, s, benzodioxane protons |
|  | = 7.35, m and 5.03, s: -$CH_2$-$\phi$ |
|  | = 3.78, s, : -$OCH_3$ |

EXAMPLE 8:
5-benzyloxy-8-isopropoxycarbonyl-1,4-benzodioxane (XIc) Code Number: 780 370

—1st step:
(5-benzyloxy-1,4-benzodioxane)yl-8-carboxylic acid (XVI) Code Number: 760 695

To a solution of 29 g (0.1 mole) of 5-benzyloxy-8-acetyl-1,4-benzodioxane (XV) obtained in the first step of Example 7, in 150 ml of pyridine were added 25.8 g (0.1 mole) of iodine. Then, the mixture was brought to 100° C. for 1 hour, the excess of pyridine was driven off, the residue was taken up in water, filtered and the precipitate obtained was put in solution in 450 ml of a 50/50 alcohol-water mixture. A solution of 70 g of soda (NaOH) in 200 ml of water was slowly added, then, washing with chloroform was carried out and the precipitate formed was filtered and dissolved in an aqueous solution of soda (NaOH). Acidification was carried out up to pH$\simeq$1 by means of hydrochloric acid, then it was concentrated and filtered. 25 g of product were obtained.
Yield: 35%
Melting point: $\simeq$200° C.
Empirical formula: $C_{16}H_{14}O_5$
Molecular weight: 286.27
Elementary analysis:

|  | C | H |
|---|---|---|
| Calculated (%) | 67.12 | 4.93 |
| Obtained (%) | 66.91 | 5.00 |

—2nd step:
5-benzyloxy-8-isopropoxycarbonyl-1,4-benzodioxane

To a toluene solution of 31 g of (5-benzyloxy-1,4-benzodioxane)yl carboxylic acid obtained in the previous step, 50 ml of thionyl chloride were added and the mixture was brought to 70°–80° C. for 2 hours. Then, the solvents were evaporated, the residue was dissolved in 200 ml of tetrahydrofuran, and 15 cm³ of isopropyl alcohol and 70 cm³ of triethylamine were added. The mixture was brought to 60° C. for 3 hours, then the precipitate formed was filtered, the filtrate evaporated and the residue chromatographed on a silica column and eluted with chloroform. 20 g of product were obtained which was recrystallized in isopropyl ether.
Yield: 71%
Melting point: 96° C.
NMR spectrum:

$\delta$ ppm = 7.38 (d), and 6.57, d, (J = 10Hz) and
4.23, s, benzodioxane protons
= 7.28, s, and 5.08 s: $CH_2$-$\phi$
= 5.09, quintet, and 1.14, d (J = 6 Hz)

—COO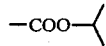

IR spectrum: 1710 and 1200 cm$^{-1}$ band:

COO

With the same method, but from the corresponding reagents, the compounds of formula XIc was prepared, given in Table III and bearing code numbers 780 366, 780 298 and 780 330.

EXAMPLE 9: (5-benzyloxy-1,4-benzodioxane)yl-8 ethyl carboxylate (XIc) Code Number: 760 696

A solution of 25 g (0.095 mole) of (5-benzyloxy-1,4-benzodioxane)yl-8-carboxylic acid obtained in the first step of Example 8, in 500 ml of alcohol and 50 ml of a solution of hydrochloric acid in 4.4 N ethanol was brought to reflux for 4 hours. Then, the solvent was evaporated, the residue was taken up in chloroform, washed with a solution of sodium bicarbonate, with water, then it was dried, and the solvent was evaporated. 26 g of ester were obtained.
Yield: 90%
IR spectrum: band at 1708 and 1200 cm$^{-1}$ (COOEt)
NMR spectrum:

$\delta$ppm = 7.22, d; 6.51, d; (J = 10Hz) and
4.38, s, : benzodioxane protons
= 7.18, s: benzylic aromatic protons
= 5.20, s: O—$CH_2$—$\phi$
= 4.35, q, and 1.35, t, (J = 8 Hz): COOEt.

EXAMPLE 10: 5-benzyloxy-8-N-cyclohexyl carboxamido-1,4-benzodioxane (XId) Code Number: 770 828

To a toluene solution of 30 g of (5-benzyloxy-1,4-benzodioxane)yl-8-carboxylic acid obtained in the first step of Example 8, were added 30 cm³ of thionyl chloride and it was brought to 70°–80° C. for 2 hours. Then, the solvents were evaporated, the residue was dissolved in 200 ml of tetrahydrofuran and 24 ml of triethylamine and 19 ml of cyclohexylamine were added. The mixture was brought to 60° C. for 3 hours and after filtration the filtrate was evaporated and the residue recrystallized in a mixture of ethyl acetate and hexane.
Yield: 82.5%
Melting point: 117° C.
Empirical formula: $C_{22}H_{25}NO_4$
Molecular weight: 367.49
Elementary analysis:

|  | C | H | N |
|---|---|---|---|
| Calculated (%) | 71.91 | 6.86 | 3.81 |
| Obtained (%) | 71.99 | 6.78 | 3.69 |

With the same method, but from the corresponding reagents, the compounds of formula XId were obtained, given in Table III and bearing the following code numbers 770 202 and 770 849.

EXAMPLE 11:
5-benzyloxy-8-N-methylcarboxamido-1,4-benzodioxane (XId) Code Number: 760 706

To a solution cooled below 0° C. of 20 g (0.07 mole) of (5-benzyloxy-1,4-benzodioxane)yl-8-carboxylic acid obtained in the 1st step of Example 8, in 200 ml of anhydrous tetrahydrofuran, 11 ml of triethylamine were added, then 6.9 ml of ethyl chloroformate. It was stirred at 0° C. for 2 hours, then a gaseous flow of methylamine was passed for 90 minutes. Then, the solution was left for one hour at room temperature, the tetrahydrofuran was evaporated, the residue was taken up in chloroform, then it was washed with water, the solvent was evaporated and recrystallized in alcohol. 18 g of product were obtained.
Yield: 80%
NMR spectrum:

| δ ppm = | 7.70, d; 6.60, d, (J = 10Hz) and 4.32, s, : benzodioxane protons |
|---|---|
| = | 5.18, s, : O—CH₂-φ |
| = | 7.36, m, —NH—CO— |
| = | 2.91, d, (J = 6Hz); CH₃—CO—N< |

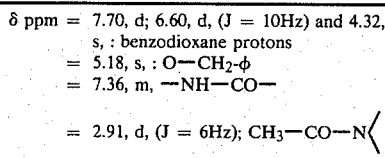

EXAMPLE 12:
5-benzyloxy-8-propionamido-1,4-benzodioxane (XIe) Code Number: 770 542

To a solution of 30 g of 5-benzyloxy-8-amino-1,4-benzodioxane (XX); code number 760 727, in 250 ml of chloroform and 21.3 ml of triethylamine, cooled to 0° C., 12.1 cm³ of propionyl chloride were slowly added. Then, it was stirred for 17 hours, washed with a solution of diluted hydrochloric acid, with water, with an aqueous solution of sodium bicarbonate, then with water, the organic phase was evaporated and the residue recrystalized in ethyl acetate.
Yield: 73%
Melting point: 139° C.
NMR spectrum:

| δ ppm = | 7.42, d; 6.51, d, (J = 10Hz) and 4.20, s: benzodioxane protons |
|---|---|
| = | 7.78, d, (J = 9Hz): —NH—CO— |
| = | 7.35, s and 5.03, s: CH₂—φ |
| = | 2.17, q, and 1.11, t (J = 7Hz): CO—CH₂—CH₃ |

IR spectrum: bands at 3400, 1670 and 1510 cm⁻¹: —NH—CO—

With the same method, but from the corresponding reagents, the compounds of formula XIe were obtained, appearing in Table III and bearing code numbers 770 689; 770 611; 770 530; 770 526 and 770 607.

EXAMPLE 13: 4-benzyloxy-2,3-methylene dioxy aniline (XXa) Code Number: 780 405

A solution of 34 g of 4-benzyloxy-2,3-methylene dioxy acetanilide (XIh), code number 780 343, in 120 ml of methanol was treated with 34 g of potassium hydroxide, for 1½ hour at reflux. Then, the precipitate formed was filtered and recrystallized in isopropyl alcohol, 13.4 g of product were obtained.
Yield: 50%
Melting point: 59° C.
NMR spectrum:

| δ ppm = | 6.22, q, (J = 9Hz) aromatic protons of the benzodioxole group |
|---|---|
| = | 5.84, s, —O—CH₂—O— |
| = | 7.36, s and 5.03, s, : —CH₂-φ |
| = | 3.17, s, —NH₂ |

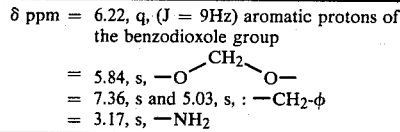

With the same method, but from the corresponding reagents, were obtained the compounds of formula (XXa), code number 780 464: 6-benzyloxy-9-amino-1,5-benzodioxepine.
Yield: 82%

Melting point: 92° C.
Empirical formula: C₁₆H₁₇NO₃
Molecular weight: 217.29
Elementary analysis:

|  | C | H | N |
|---|---|---|---|
| Calculated (%) | 70.89 | 6.32 | 5.16 |
| Obtained (%) | 70.72 | 6.39 | 5.13 | as well as the compound of formula (XX), code number 760 727: 5-benzyloxy-8-amino-1,4-benzodioxane:
Yield: 78%
Melting point: 130° C.
Empirical formula: C₁₅H₁₅NO₃
Molecular weight: 257.28
Elementary analysis:

|  | C | H | N |
|---|---|---|---|
| Calculated (%) | 70.02 | 5.88 | 5.44 |
| Obtained (%) | 69.73 | 5.94 | 5.24 |

EXAMPLE 14: 4-benzyloxy-2,3-methylene dioxy-2,3-acetanilide (XIh) Code Number: 780 343

To a suspension of 100 g of 4-benzyloxy-2,3-methylene dioxy-2,3 acetophenone oxime (XXII), code number 780 342, in 500 ml of acetic acid, 500 ml of acetic anhydride were slowly added, then a gaseous flow of hydrochloric acid was passed at 10° C., for 1 hour. Then, the solution was brought to 40°-50° C. for 5 hours, the solvents were evaporated, the residue was taken up with chloroform, then it was washed with water, the solvent was evaporated and the residue recrystallized in ethyl acetate.
Yield: 84%
Melting point: 148° C.
NMR spectrum:

| δ ppm = | 7.18, m and 5.18 s : —CH₂φ |
|---|---|
| = | 7.18, m (aromatic protons of the benzodioxole nucleus and of CH₂φ) |
| = | 5.95, s, : —O—CH₂—O— |
| = | 2.09, s, CH₃—CO—N— |
| = | 6.51 d, (J = 9Hz) : NH—CO— |

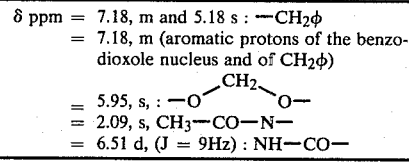

IR spectrum: 3260, 1650 cm⁻¹: band —NH—CO—

With the same method but from the corresponding reagents, the compound of formula (XIh) was obtained, code number 780 463, appearing in Table III.

EXAMPLE 15: 4-benzyloxy-2,3-methylene dioxy acetophenone oxime (XXII) Code Number: 780 342

A solution of 192 g of 4-benzyloxy-2,3-methylene dioxy acetophenone (XIi); code number 780 305 and of 64 g of hydroxylamine hydrochloride in 500 ml of pyridine and 500 ml of ethanol were brought to reflux for 2 hours. Then, the solvents were evaporated, the residue was taken up in water and the precipitate formed was filtered.
Yield: 98%
Melting point: 168° C.
Empirical formula: C₁₆H₁₅NO₄
Molecular weight: 285.29
Elementary analysis:

| | C | H | N |
|---|---|---|---|
| Calculated (%) | 67.36 | 5.30 | 4.91 |
| Obtained (%) | 67.31 | 5.30 | 4.91 |

With the same method, but from the corresponding reagents, 6-benzyloxy-9-acetyl-1,5-benzodioxepine oxime (XXII) was obtained, code number 780 390.
Yield: 90%
Melting point: 134° C.
NMR Spectrum:

$\delta$ ppm = 13.00, m, = N—OH
= 6.51, d; 6.88, d, (J = 10Hz); 4.10, m; and 2.08, m: benzodioxepine protons
= 5.17 s and 7.19, s: CH$_2$—$\phi$
= 2.20, s: —CH$_3$

EXAMPLE 16:
5-benzyloxy-8-acetamido-1,4-benzodioxane (XIh) Code Number: 760 606

Following the working method described in the first step of Example 7, but from 5-hydroxy-8-acetamido-1,4-benzodioxane (VIIm), code number 750 548, 91% of product was obtained.
Melting point: 148° C.
NMR spectrum:

$\delta$ ppm = 7.35, d; 6.56, d, (J = 10Hz) and 4.24, s, benzodioxane protons
= 7.36, s, and 5.07, s, : CH$_2$—$\phi$
= 7.76, d, (J = 9Hz): NH—CO—
= 2.17, s, : CH$_5$ IR spectrum: bands at 3270, and 1660 cm$^{-1}$: —NH—CO—CH$_3$

EXAMPLE 17: 5-benzyloxy-8-N-ethyl carbamoyl amino-1,4-benzodioxane (XIf) Code Number: 770 304

For 20 hours a mixture of 25 g of 5-benzyloxy-8-amino-1,4-benzodioxane, code number 760 727, and 8 ml of ethyl isocyanate in 300 ml of chloroform was maintained at reflux. Then, the solvents were evaporated in a vacuum and the residue recrystallized in ethanol.
Yield: 80%
Melting point: 188° C.
NMR spectrum:

$\delta$ ppm = 7.41, d; 6.56, d, (J = 10Hz) and 4.19, s, benzodioxane protons
= 7.38, s, and 4.97, s, : —CH$_2$—$\phi$
= 6.60, m and 7.40, m: NH—CO—NH
= 3.02, q and 1.00, t, (J = 7Hz): —CH$_2$—CH$_3$—

With the same method, but from the corresponding reagents, the compounds of formula (XIf) were obtained, appearing in Table III and bearing the code numbers 770 074, 770 480, 770 627, 770 631, 770 708, 770 078, 770 082, 770 220, 780 406 and 780 465.

EXAMPLE 18: 5-benzyloxy-8-ethoxy carbonylamino-1,4-benzodioxane (XIg) Code Number: 770 522

To a solution of 30 g of 5-benzyloxy-8-amino-1,4-benzodioxane (XX), code number 760 727, in 250 ml of chloroform, 21.3 ml of triethylamine, then slowly, at 0° C., 15.2 g of ethyl chloroformate were added. The solution was stirred for 7 hours, filtered and the filtrate was washed with a diluted hydrochloric acid solution, with water, with a solution of sodium bicarbonate and with water. The solvent was evaporated and the residue recrystallized in ethylacetate.
Yield: 74%
Melting point: 108° C.
NMR spectrum:

$\delta$ ppm = 6.52, d; 7.41, d, (J = 10Hz) and 4.22, s, : benzodioxane protons
= 7.38, s and 5.08, s : CH$_2$—$\phi$
= 4.10, q, and 1.14, t, (J = 7Hz): CH$_2$—CH$_3$
= 6.80, s, —NH—

IR spectrum: 3315 and 1692 cm$^{-1}$=NHCOOEt

EXAMPLE 19: 4-benzyloxy-2,3-methylene dioxy acetophenone (XIi) Code Number: 780 305

A mixture of 140 g of 4-benzyloxy-2,3-dihydroxy acetophenone (XXIV), code number 780 304, 295 g of diiodomethane and 300 g of potassium carbonate in 1200 ml of dimethyl formamide was brought to reflux for 5 hours. After filtering, the filtrate was evaporated, the residue was taken up in a 50/50 mixture of ethyl acetate and ether, then it was washed with water, the organic phase was evaporated and the residue was crystallized in ethanol.
Yield: 93%
Melting point: 101° C.
NMR spectrum:

IR spectrum: 1670 cm$^{-1}$: —CO—CH$_3$

With the same method, but from the corresponding reagents, the compound (XIi), code number 780 238, given in Table III, was obtained.

EXAMPLE 20: 4-benzyloxy-2,3-dihydroxy acetophenone (XXIV) Code Number: 780 304

A mixture of 349 g of gallacetophenone, 1750 g of sodium bicarbonate and 260 g of benzyl chloride in 4000 ml of acetone were stirred for 2 hours at room temperature. Then the mixture was brought to reflux for 36 hours, filtered, the solvent was evaporated and the residue was taken up in ethyl acetate and diluted in isopropyl ether. 58% of crystallized product were obtained.
Melting point: 128° C.
Empirical formula: C$_{15}$H$_{14}$O$_4$
Molecular weight: 258.26
Elementary analysis:

|  | C | H |
|---|---|---|
| Calculated (%) | 69.75 | 5.46 |
| Obtained (%) | 69.48 | 5.60 |

EXAMPLE 21 : 5-benzyloxy-8-N,N'-dimethyl carbamoyl amino-1,4-benzodioxane (XIj) Code Number: 771 235

—First step:
5-benzyloxy-8-N-methylamino-1,4-benzodioxane (XXV) Code Number: 771 234

A mixture of 40 g of 5-benzyloxy-8-amino-1,4-benzodioxane (XX), code number 760 727, 120 ml of formaldehyde (at 38% in an aqueous solution) and 29 g of 5,5-dimethylhydantoin in 300 ml of ethanol was brought to reflux for 12 hours. Then the solvent was evaporated, the residue was taken up in chloroform and washed by means of a diluted hydrochloric acid solution. The organic phase was evaporated and the residue dissolved in 500 ml of dimethylsulfoxide. 23 g of sodiumborohydride were slowly added, and brought to 100° C. for 30 minutes. Then it was diluted in 1500 ml of water, extracted with chloroform, washed with water and the solvent evaporated. The residue was chromatographed on a silica column. Eluted with chloroform, 34% of product was obtained.

Melting point: 62° C.
Empirical formula: $C_{16}H_{17}NO_3$
Molecular weight: 271.30
Elementary analysis:

|  | C | H | N |
|---|---|---|---|
| Calculated (%) | 70.83 | 6.32 | 5.16 |
| Obtained (%) | 70.70 | 6.29 | 4.90 |

—Second step: 5-benzyloxy-8-N,N'-dimethyl carbamoyl amino-1,4-benzodioxane

A mixture of 22.4 g of 5-benzyloxy-8-N-methyl amino-1,4-benzodioxane, obtained from the preceding step, and 10 ml of methyl isocyanate in 100 ml of chloroform were brought to reflux for 2 hours, then the solvent was evaporated and the residue recrystallized in alcohol:

Yield: 74%
Melting point: 140° C.
Empirical formula: $C_{18}H_{20}N_2O_4$
Molecular weight: 328.36
Elementary analysis:

|  | C | H | N |
|---|---|---|---|
| Calculated (%) | 65.84 | 6.14 | 8.53 |
| Obtained (%) | 65.71 | 6.07 | 8.62 |

EXAMPLE 22:
5-benzyloxy-8-morpholinocarbonylamino-1,4-benzodioxane (XIk) Code Number: 771 146

A mixture of 38 g of 5-benzyloxy-8-ethoxycarbonylamino-1,4-benzodioxane (XIg), code number 770 522, and 300 ml of morpholine was brought to reflux for 16 hours, in the presence of a pinch of ammonium chloride. Then the morpholine in excess was evaporated and the residue was recrystallized in 96° ethanol.

Yield: 72%
Melting point: 184° C.
Empirical formula: $C_{20}H_{22}N_2O_5$
Molecular weight: 370.39
Elementary analysis:

|  | C | H | N |
|---|---|---|---|
| Calculated (%) | 64.85 | 5.67 | 7.56 |
| Obtained (%) | 64.85 | 5.95 | 7.74 |

EXAMPLE 23:
5-benzyloxy-8-N,N-dimethylcarbamoyl amino-1,4-benzodioxane (XII) Code Number: 771 230

To a solution of 100 g of 5-benzyloxy-8-amino-1,4-benzodioxane (XX), code number 760 727, and 100 ml of triethylamine, in 1000 ml of chloroform were slowly added 47 ml of dimethylcarbamoyl chloride, at room temperature, then it was brought to reflux for 48 hours. After filtering, the filtrate was evaporated and the residue was recrystallized in ethanol. 60 g of product were obtained.

Yield: 47%
Melting point: 142° C.
Empirical formula: $C_{18}H_{20}N_2O_4$
Molecular weight: 328.36
Elementary analysis:

|  | C | H | N |
|---|---|---|---|
| Calculated (%) | 65.84 | 6.14 | 8.53 |
| Obtained (%) | 65.67 | 6.35 | 8.25 |

EXAMPLE 24:
5-benzyloxy-8-cyanomethyl-1,4-benzodioxane (XIm) Code Number: 770 119

—First step:
5-benzyloxy-8-chloromethyl-1,4-benzodioxane (XXVI) Code Number: 770 188

To a solution, cooled to −10° C., of 10 g (0.037 mole) of 5-benzyloxy-8-hydroxymethyl-1,4-benzodioxane (XIp), code number 760 701, in 100 ml of chloroform were slowly added 4.6 g (0.039 mole) of thionyl chloride. They were left in contact for 15 minutes, then the solvents were evaporated, the residue was taken up in chloroform, washed with a solution of sodium bicarbonate, dried and the solvent was evaporated. 10.4 g of unstable product were obtained which, after checking by chromatography on a thin silica layer, was used in the synthesis of the compound of formula (XIm), code number 770 119.

—Second step:
5-benzyloxy-8-cyanomethyl-1,4-benzodioxane

A solution of 99 g (0.34 mole) of 5-benzyloxy-8-chloromethyl-1,4-benzodioxane, obtained in the previous step, 19 g (0.4 mole) of sodium cyanide and 0.5 g of sodium iodide in 1000 ml of anhydrous dimethylformamide was brought to 60° C. for 45 minutes. Then the solvent was driven off in a vacuum, the residue was taken up in 600 ml of a saturated solution of sodium bicarbonate and 300 ml of chloroform, the organic phase was decanted, dried and the solvent evaporated. 85 g of product were obtained.
Yield: 89%
Melting point: 95° C.
Empirical formula: $C_{17}H_{15}NO_3$
Molecular weight: 281.29
Elementary analysis:

|  | C | H | N |
|---|---|---|---|
| Calculated (%) | 72.58 | 5.18 | 4.98 |
| Obtained (%) | 72.15 | 5.47 | 4.84 |

EXAMPLE 25:
5-benzyloxy-8-carboxamidomethyl-1,4-benzodioxane (XIn) Code Number: 770 383

To a solution of 50 g of 5-benzyloxy-8-cyanomethyl-1,4-benzodioxane, obtained in the process of Example 24, in 250 ml of t-butanol were slowly added 39 g of pulverized potassium hydroxide, then it was brought to reflux for 20 minutes. Then the mixture was poured into 500 ml of an aqueous solution of sodium chloride, extracted with chloroform, washed with water, the solvent was evaporated and the residue recrystallized in ethanol.
Yield: 90%
Melting point: 166° C.
NRM spectrum:

| $\delta$ ppm = 6.51, d; 6.72, d; (J = 10Hz) and 4.30, s,: benzodioxane protons |
|---|
| = 7.37, s, and 5.16, s = $CH_2-\phi$ |
| = 5.76 m : $-COCH_2$ |
| = 3.43, s, : $-CH_2-CO-$ |

EXAMPLE 26:
5-benzyloxy-8-N-methylcarboxamidomethyl-1,4-benzodioxane (XIo) Code Number: 770 379

—First step: 2-[(5-benzyloxy-1,4-benzodioxane)yl-5] acetic acid (XXVII) Code Number: 770 308

To a solution of 57 g of sodium hydroxide in 1 l of 50% aqueous ethanol, cooled to 0° C., were added 200 g of 5-benzyloxy-8-cyanomethyl-1,4-benzodioxane, obtained with the process of Example 24, then the ethanol was distilled; a solution of hydrochloric acid was added up to acid pH, it was washed with chloroform, acidified up to pH=3 and filtered.
Yield: 78%
Melting point: 150° C.
NMR spectrum:

| $\delta$ ppm = 6.43, d; 6.65, d, and 4.23, s, : benzodioxane protons |
|---|
| = 7.38, s, and 5.08, s, : $-CH_2-\phi$ |
| = 3.58, s, : $-CH_2-COO-$ |
| = 9.20, m. $-COOH$ |

—Second step:
5-benzyloxy-8-N-methylcarboxamidomethyl-1,4-benzodioxane

To a solution of 80 g of 2-[(5-benzyloxy-1,4-benzodioxane)yl-5] acetic acid obtained in the preceding step, in 500 ml of dimethyl formamide, cooled to 0° C., 50 ml of triethylamine were added, then 31 ml of ethyl chloroformate. Then a gaseous flow of methylamine was passed and the reaction was checked by chromatography on a thin silica layer. Then it was poured into iced water, the precipitate formed was filtered and taken up in chloroform. The organic phase was washed with a diluted hydrochloric acid solution, the organic phase was evaporated and the residue recrystallized in ethyl acetate. 70 g of product were obtained.
Yield: 85%
Melting point: 160° C.
NMR spectrum:

| $\delta$ ppm = 6.02, d, 6.23, d (J = 9Hz) and 3.82, s, : benzodioxane protons |
|---|
| = 6.94, s and 4.63, s, : $-CH_2-\phi$ |
| = 3.02, s, : $CH_2-CO-$ |
| = 2.30, d, (J = 5Hz): $-CH_3$ |
| = 5.12, m, $-NH-$ |

IR spectrum: 3295 and 1640 cm$^{-1}$: $-CONH-$

EXAMPLE 27:
5-benzyloxy-8-hydroxymethyl-1,4-benzodioxane (XIp) Code Number: 760 701

A solution of 12.8 g (0.04 mole) of (5-benzyloxy-1,4-benzodioxane)yl ethyl carboxylate, obtained according to the method of Example 9, in 50 ml of anhydrous tetrahydrofuran was added to a suspension of 1.54 g (0.04 mole) of lithium hydride and aluminum in 150 ml of tetrahydrofuran and left at room temperature for 30 minutes. Then it was hydrolyzed with an aqueous solution of sodium sulfate then with a saturated aqueous solution of sodium sulfate, filtered, the solvent was evaporated and the residue recrystallized in benzene. 11 g of product were thus obtained.
Yield: 97%
Melting point: 106° C.
NMR spectrum:

| $\delta$ ppm = 6.78, d; 6.51, d; (J = 10Hz) and 4.24, s, : benzodioxane protons |
|---|
| = 7.32, s, and 5.12, s; : $-CH_2-\phi$ |
| = 4.60 m, and 2.20 m, : $-CH_2OH$ |

EXAMPLE 28: 5-benzyloxy-8-cyano-1,4-benzodioxane (XIq) Code Number: 770 582

To a solution of 84.5 g of 5-benzyloxy-8-carboxamido-1,4-benzodioxane (XId), code number 770 202, obtained by the method of Example 10, in 1000 ml of benzene, were added 80 g of phosphorous pentachloride. The temperature rises to 40° C. after 45 minutes, the solvent was evaporated, and the residue was taken up in toluene, washed with water and the solvent was evaporated. The residue was recrystallized in ethyl acetate.
Yield: 62%
Melting point: 145° C.
NMR spectrum:

| $\delta$ ppm = 6.50, d, 7.01, d, (J = 10Hz) and 4.25, s,: benzodioxane protons |
|---|
| = 7.38 s, and 5.05 s, : $CH_2-\phi$ |

IR spectrum: 2210 cm$^{-1}$: band $-CN$

EXAMPLE 29:
5-benzyloxy-8-ethoxycarbonylmethyl-1,4-benzodioxane (XIr) Code Number: 770 309

To a solution of 72 g of 2-[(5-benzyloxy-1,4-benzodioxane)yl-8] acetic acid, obtained by the method of the first step of Example 26, in 200 ml of ethanol, were added 100 ml of hydrochloric acid in ethanol 7.5 N, then it was brought to reflux for 30 minutes. The solvent was evaporated, the residue was taken up in chloroform, then it was washed with a saturated sodium bicarbonate solution, with water, and the solvent was evaporated. 98% of crystallized product was obtained.
Melting point: 86° C.
NMR spectrum:

$\delta$ ppm = 6.40, d; 6.61, d (J-10Hz) and 4.18, s,: benzodioxane protons
= 7.36, m, and 5.03, s: —CH$_2$—$\phi$
= 3.37, s: —CH$_2$—COO
= 4.18, q and 1.10, t, (J = 8Hz) : —COO—CH$_2$—CH$_3$

TABLE II

H—X'—Ar'

| Code Number | X' | —Ar' | Empirical Formula | Molecular Weight | Melting Point °C. | Yield % | IR or NMR spectrum or elementary analysis |
|---|---|---|---|---|---|---|---|
| 780 387 | S | (benzodioxane) | C$_8$H$_8$O$_2$S | 168.210 | oil | 85 | NMR (CDCL$_3$) 6.68,m 3 aromatic protons 4.18,s 4 dioxane protons 3.78, s SH |
| 780 382 | S | (benzodioxane)-COCH$_3$ | C$_{10}$H$_{10}$O$_3$S | 210.246 | 78 | 90 | Elementary analysis<br>   C    H<br>Calc. % 57.12 4.79<br>Obt. % 57.15 4.66 |
| 760 707 | oxygen | (benzodioxane)-CONHCH$_3$ | C$_{10}$H$_{11}$NO$_4$ | 209.196 | 200 | 92 | Elementary analysis<br>   C    H    N<br>Calc. % 57.41 5.30 6.70<br>Obt. % 57.32 5.39 6.65 |
| 780 002 | oxygen | (benzodioxane)-OCOCH$_3$ | C$_{10}$H$_{10}$O | 210.18 | oil | 100 | NMR (CDCl$_3$) 6.41,s & 4.17,s (6 benzodioxane protons) $\delta$ppm 5.55, s (OH) 2.23, s (OCOCH$_3$) |
| 770 583 | oxygen | (benzodioxane)-CN | C$_9$H$_7$NO$_3$ | 177.154 | 165 | 95.5 | NMR (CDCl$_3$) 7.08,d (J = 10Hz); $\delta$ppm 6.5,d (J = 10Hz) & 4.35,s (6 benzodioxane protons) 9.35,s OH |
| 770 523 | oxygen | (benzodioxane)-NHCOOC$_2$H$_5$ | C$_{11}$H$_{13}$NO$_5$ | 239.22 | 123 | 70 | Elementary analysis<br>   C    H    N<br>Calc. % 55.22 5.48 5.86<br>Obt. % 55.27 5.17 5.95 |

TABLE II-continued

H—X'—Ar'

| Code Number | X' | —Ar' | Empirical Formula | Molecular Weight | Melting Point °C. | Yield % | IR or NMR spectrum or elementary analysis |
|---|---|---|---|---|---|---|---|
| 780 371 | oxygen | benzodioxane—COO—iPr | $C_{12}H_{15}O_5$ | 238.232 | 125 | 87 | NMR (CDCl$_3$) 7.4,d (J = 10Hz); δppm 6.5,d (J = 10Hz) & 4.45,s (6 benzodioxane protons) 6.8 s OH 5.2, q (J = 6Hz); 1.35,d (J = 6Hz) COO—⟨ |
| 780 367 | oxygen | benzodioxane—COO+ | $C_{13}H_{16}O_5$ | 252.288 | 156 | 94 | NMR (CDCl$_3$) 7.4,d (J = 10Hz); δppm 6.5,d (J = 10Hz) & 4.3,s (6 benzodioxane protons) 6.35 s OH 1.57 s COO+ |
| 780 299 | oxygen | benzodioxane—COOC$_5$—H$_{11}$n | $C_{14}H_{18}O_5$ | 266.284 | 45 | 100 | NMR (CDCl$_3$) 7.38,d (J = 10Hz); δppm 6.48,d (J = 10Hz) & 4.22,s (6 benzodioxane protons) 0.75 to 2.0 massive (COOC$_5$H$_{11}$n) |
| 780 331 | oxygen | benzodioxane—COO—cyclohexyl | $C_{15}H_{18}O_5$ | 278.294 | 114 | 100 | NMR (CDCl$_3$) 7.4,d (J = 10Hz); δppm 6.48,d (J = 10Hz) & 4.26,s (6 benzodioxane protons) 6.45 s OH 1.2 to 2.2 massive -COO—⟨⟩ |
| 770 203 | oxygen | benzodioxane—CONH$_2$ | $C_9H_9NO_4$ | 195.17 | 220 | 97.5 | NMR (DMSO) 7.45,d (J = 10Hz); δppm 6.5,d (J = 10Hz) & 4.38,s (6 benzodioxane protons) 7.4,s CONH$_2$ |
| 770 829 | oxygen | benzodioxane—CONH—cyclohexyl | $C_{15}H_{19}NO_4$ | 277.310 | 182 | 92 | NMR (DMSO) 7.31,D (J = 10Hz); δppm 6.45,d (J = 10Hz) & 4.39,s (6 benzodioxane protons) 10.0 s (OH) 7.6,d & 1.0 to 2.0 massive CONH—⟨⟩ |
| 770 850 | oxygen | benzodioxane—CONH—phenyl | $C_{15}H_{13}NO_4$ | 271.262 | 163 | 100 | NMR (DMSO) 7.4,m & 6.45d δppm (aromatic protons) 4.35 m (4 dioxane protons) 9.83 s (OH) |
| 770 543 | oxygen | benzodioxane—NH—COEt | $C_{11}H_{13}NO_4$ | 223.222 | 190 | 90 | NMR (DMSO) 7.08,d (J = 10Hz); δppm 6.3,d (J = 10Hz) & 4.24,s (6 benzodioxane protons) 9.3,s & 8.9 s OH & NH 2.32q (J = 7Hz) & 1.09,d (J = 7Hz) CO Et |

TABLE II-continued

H—X'—Ar'

| Code Number | X' | —Ar' | Empirical Formula | Molecular Weight | Melting Point °C. | Yield % | IR or NMR spectrum or elementary analysis |
|---|---|---|---|---|---|---|---|
| 770 608 | oxygen | benzodioxane—NH—CO—$C_3H_7$ (n) | $C_{12}H_{15}NO_4$ | 237.248 | 118 | 94 | NMR (DMSO) 7.1,d (J = 10Hz); δppm 6.3,d (J = 10Hz) & 4.2,s (6 benzodioxane protons) 9.0 s & 8.8 s OH & NH 2.3 m; 1.4 m & 0.92,t (J = 6Hz) $COC_3H_7$n |
| 770 599 | oxygen | benzodioxane—$NHCOC_4H_9$ (n) | $C_{13}H_{17}NO_4$ | 251.284 | 80 | 100 | NMR (DMSO) 7.15,d (J = 10Hz); δppm 6.35,d (J = 10Hz) & 4.2 s (6 benzodioxane protons) 9.0 s OH & NH 2.35 m; 0.8 to 1.8 massive $COC_4H_9$n |
| 770 690 | oxygen | benzodioxane—NH—CO—iPr | $C_{12}H_{15}NO_4$ | 237.248 | 55 | 100 | NMR (DMSO) 7.1,d (J = 10Hz); δppm 6.32,d (J = 10Hz) & 4.2,s (6 benzodioxane protons) 9.1,s & 8.7,s OH & NH 2.65,m & 1.05,d (J = 7Hz) CO—⟨ |
| 770 612 | oxygen | benzodioxane—NH—CO—tBu | $C_{13}H_{17}NO_4$ | 251.284 | 54 | 90 | NMR (DMSO) 7.02,d (J = 10Hz); δppm 6.35,d (J = 10Hz) & 4.22,s (6 benzodioxane protons) 9.7 s & 8.2,s OH & NH 1.20,s CO+ |
| 770 531 | oxygen | benzodioxane—NH—CO—cyclohexyl | $C_{15}H_{19}NO_4$ | 277.31 | 68 | 100 | NMR (DMSO) 7.12,d (J = 10Hz); δppm 6.35,d (J = 10Hz) & 4.21,s (6 benzodioxane protons) 9.0 s & 8.7,s OH & NH 1.0 to 2.0, massive CO—⟨⟩ |
| 770 527 | oxygen | benzodioxane—NH—CO—Ph | $C_{15}H_{13}NO_4$ | 271.262 | 84 | 95 | NMR (DMSO) 6.95,d (J = 10Hz); δppm 6.42,d (J = 10Hz) 4.23,s (6 benzodioxane protons) 10.6,s & 9.65,s OH & NH 7.95,m & 7.5 m CO—Ph |
| 770 305 | oxygen | benzodioxane—NH—CONH—Et | $C_{11}H_{14}N_2O_4$ | 238.238 | 170 | 98 | NMR (DMSO) 7.3,d (J = 10Hz); δppm 6.32,d (J = 10Hz) & 4.25,s (6 benzodioxane protons) 8.7,s (OH) 7.45,s; 6.55,m, 3.1,m & 1.05,t (J = 7Hz) NHCONH Et |
| 770 481 | oxygen | benzodioxane—NHCO—NH$C_3H_7$ (n) | $C_{12}H_{16}N_2O_4$ | 252.264 | 186 | 85 | NMR (DMSO) 7.3,d (J = 10Hz); δppm 6.3,d (J = 10Hz) & 4.21,s (6 benzodioxane protons) 8.83,s (OH) 7.5,s; 6.55,m; 3.05m & 1.1,m NHCONH$C_3H_7$n |

TABLE II-continued

H—X'—Ar'

| Code Number | X' | —Ar' | Empirical Formula | Molecular Weight | Melting Point °C. | Yield % | IR or NMR spectrum or elementary analysis |
|---|---|---|---|---|---|---|---|
| 770 628 | oxygen | benzodioxane-NHCO-NH-iPr | $C_{12}H_{16}N_2O_4$ | 252.264 | 189 | 77 | NMR (DMSO) 7.3,d (J = 10Hz); δppm 6.3,d (J = 10Hz) & 4.22,s (6 benzodioxane protons) 8.7,s (OH) 7.4,s; 6.42, m; 3.75m & 1.1,d (J = 7Hz) NHCONH—⟨ |
| 770 632 | oxygen | benzodioxane-NHCO-NHC$_4$H$_9$ (n) | $C_{13}H_{18}N_2O_4$ | 266.290 | 195 | 98 | NMR (DMSO) 7.32,d (J = 10Hz); δppm 6.28,d (J = 10Hz) & 4.25,s (6 benzodioxane protons) 9.1,s (OH) 7.42,s; 6.52,s 3.05,m; 1.38,m & 0.9,m NHCONHC$_4$H$_9$n |
| 770 709 | oxygen | benzodioxane-NHCONH+ | $C_{13}H_{18}N_2O_4$ | 266.290 | 199 | 99 | NMR (DMSO) 7.32,d (J = 10Hz); δppm 6.3,d (J = 10Hz) & 4.23,s (6 benzodioxane protons) 7.4,s; 6.5,s & 1.27,s NHCONH+ |
| 780 221 | oxygen | benzodioxane-NHCO-NH-C$_6$H$_4$-OCH$_3$ | $C_{16}H_{16}N_2O_5$ | 316.304 | 232 | 87 | Elementary analysis<br>    C    H    N<br>Calc. % 60.75 5.10 8.86<br>Obt. % 60.65 5.17 8.61 |
| 771 231 | oxygen | benzodioxane-NHCO-N(CH$_3$)$_2$ | $C_{11}H_{14}N_2O_4$ | 238.238 | 176 | 75 | Elementary analysis<br>    C    H    N<br>Calc. % 55.45 5.92 11.76<br>Obt. % 55.61 5.75 11.84 |
| 771 147 | oxygen | benzodioxane-NHCO-morpholine | $C_{13}H_{16}N_2O_5$ | 280.274 | 172–4 | 83 | NMR (CDCl$_3$) 7.38,d (J = 10Hz); δppm 6.48,d (J = 10Hz) & 4.32,s (6 benzodioxane protons) 7.3,s & 6.5,s OH & NH 3.75,m & 3.5,m —N⟨O⟩ |
| 771 236 | oxygen | benzodioxane-N(CH$_3$)-CONHCH$_3$ | $C_{11}H_{14}N_2O_4$ | 238.238 | 235 | 70 | Elementary analysis<br>    C    H    N<br>Calc. (%) 55.45 5.92 11.76<br>Obt. (%) 55.41 6.28 11.82 |
| 770 310 | oxygen | benzodioxane-CH$_2$COOEt | $C_{12}H_{14}O_5$ | 238.232 | oil | 98 | NMR (CDCl$_3$) 6.65,d (J = 10Hz); δppm 6.40,d (J = 10Hz) & 4.20,s (6 benzodioxane protons) 7.32,s (OH) 4.18,q (J = 6Hz); 3.51,s & 1.12,t (J = 6Hz) CH$_2$ CO$_2$ Et |

TABLE II-continued

H—X'—Ar'

| Code Number | X' | —Ar' | Empirical Formula | Molecular Weight | Melting Point °C. | Yield % | IR or NMR spectrum or elementary analysis |
|---|---|---|---|---|---|---|---|
| 770 384 | oxygen | 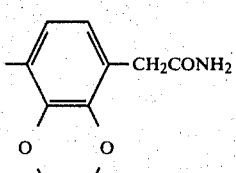 | C₁₀H₁₁NO₄ | 209.196 | 190 | 95 | NMR (DMSO) 6.52,d (J = 10Hz); δppm 6.3,d (J = 10Hz) & 4.18,s (6 benzodioxane protons) 6.65 to 7.2 massive CONH₂ 3.20,s - CH₂CO |
| 770 380 | oxygen | 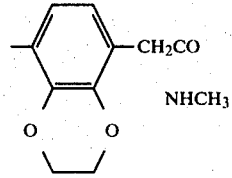 | C₁₁H₁₃NO₄ | 223.222 | 170-5 | 98 | NMR (DMSO) 6.6,d (J = 10Hz); δppm 6.35,d (J = 10Hz) & 4.22,s (6 benzodioxane protons) 8.15,s & 7.55 m OH & NH 3.3,s CH₂CO 2.6,d (J = 5Hz) CONHCH₃ |
| 780 306 | oxygen | 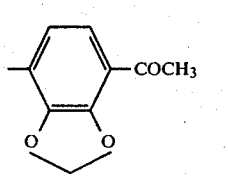 | C₉H₈O₄ | 180.184 | 191 | 100 | Elementary analysis<br>　　　　C　　H<br>Calc. (%) 60.00 4.48<br>Obt. (%) 60.30 4.66 |
| 780 344 | oxygen | 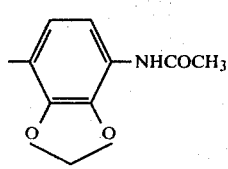 | C₉H₉NO₄ | 195.170 | 212 | 100 | Elementary analysis<br>　　　　C　　H　　N<br>Calc. (%) 55.38 4.65 7.18<br>Obt. (%) 55.17 4.47 7.10 |
| 780 407 | oxygen | 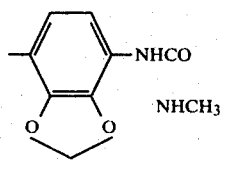 | C₉H₁₀N₂O₄ | 210.186 | 236 | 92.5 | Elementary analysis<br>　　　　C　　H　　N<br>Calc. (%) 51.43 4.79 13.33<br>Obt. (%) 51.19 4.65 13.40 |
| 780 239 | oxygen | 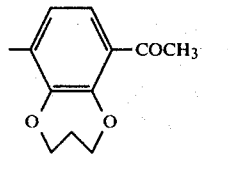 | C₁₁H₁₂O₄ | 208.206 | 121 | 43 | Elementary analysis<br>　　　　C　　H<br>Calc. (%) 63.45 5.81<br>Obt. (%) 63.54 5.89 |
| 780 391 | oxygen | 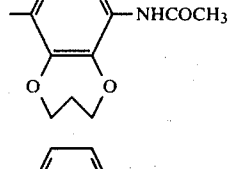 | C₁₁H₁₃NO₄ | 223.222 | 177 | 51 | NMR (DMSO) 7.32,d (J = 10Hz); δppm 6.43,d (J = 10Hz) 4.05,m & 2.05,m (8 benzodioxepine protons) 8.15,b & 7.3,b OH & NH 2.05,s COCH₃ |
| 780 466 | oxygen | 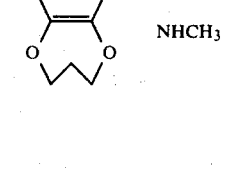 | C₁₁H₁₄N₂O₄ | 238.228 | 182 | 95 | NMR (DMSO) 7.5,d (J = 10Hz); δppm 6.45,d (J = 10Hz) 4.05,m & 2.1m (8 benzodioxepine protons) 8.3,b; 7.63,s & 6.55,m OH & NHCONH 2.65,d (J = 4Hz) CH₃ |

TABLE II-continued

H—X'—Ar'

| Code Number | X' | —Ar' | Empirical Formula | Molecular Weight | Melting Point °C. | Yield % | IR or NMR spectrum or elementary analysis |
|---|---|---|---|---|---|---|---|
| 760 697 | oxygen | benzodioxane-COOEt | $C_{11}H_{12}O_5$ | 224.206 |  | 100 | δppm = 7.40; 6.50; d; (J = 10Hz) & 4.28,s benzodioxane protons = 6.35m; —OH = 4.31,q, & 1.34,t,(J = 8Hz): COOEt IR: bands at 1710 & 1200 cm$^{-1}$ (COOEt) |
| 770 075 | oxygen | benzodioxane-NHCO-NH-CH₃ | $C_{10}H_{12}N_2O_4$ | 224.212 | 218 | 85 | δppm = 7.30; 6.30; d,(J = 10Hz); 4.22,s,: benzodioxane protons = 7.60,s, & 6.43,d (J = 5Hz): —NHCONH— = 2.60,d,(J = 5Hz): —CH₃ |
| 770 079 | oxygen | benzodioxane-NHCO-NH-cyclohexyl | $C_{15}H_{20}N_2O_4$ | 292.326 | 235 | 90 | δppm = 7.32, 6.38; d,(J = 10Hz); 4.30,s: benzodioxane protons = 7.43,s, & 6.52,d,(J = 5Hz): —NH—CO—NH— = 1.5,m, —⬡ |
| 770 083 | oxygen | benzodioxane-NHCO-NH-phenyl | $C_{15}H_{15}N_2O_4$ | 286.27 | 215 | 93 | δppm = 7.32; & 6.38; d,(J = 10 Hz); 4.32,s,: benzodioxane protons = 9.01,s, & 7.82,s,—NH—CO—NH— = 7.6 a 6.8,m,: —⬡ |
| 760 702 | oxygen | benzodioxane-CH₂OH | $C_9H_{11}O_4$ | 182.17 | 136 | 96.5 | δppm = 6.72,6.50,d,(J = 10Hz); 4.20s: benzodioxane protons = 4.38,s,: —CH₂—OH = 5.50,m,: —OH |
| 770 185 | oxygen | benzodioxane-CH₂—CN | $C_{10}H_{10}NO_3$ | 191.180 | oil | 94 | δppm = 6.72,6.52d,(J = 10Hz), 4.23,s,: benzodioxane protons = 3.45,s,—CH₂—CN |

TABLE III

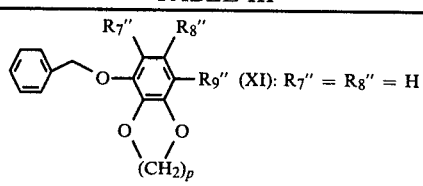

R₇'' R₈''
⬡—O— benzene —R₉''   (XI): R₇'' = R₈'' = H
     O   O
      (CH₂)ₚ

| Code Number | p | —R₉'' | | Empirical Formula | Molecular Weight | Melting Point °C. | Yield % | IR or NRM spectrum or elementary analysis |
|---|---|---|---|---|---|---|---|---|
| 780 366 | 2 | —COO + | XI$_c$ | $C_{20}H_{22}O_5$ | 342.376 | 90 | 58 | NMR (CDCl₃) δ ppm = 7.35,d (J = 10Hz) 6.48,d(J = 10Hz) & 4.35,s (6 benzodioxane protons) 7.38,s & 5.18,s O—CH₂—⬡ 1.55,s COO + |
| 780 298 | 2 | —COO—C₅H₁₁ (n) | XI$_c$ | $C_{21}H_{24}O_5$ | 356.402 | 50 | 94 | NMR (CDCl₃) δ ppm = 7.35,d |

TABLE III-continued $$\text{(XI)}: R_7'' = R_8'' = H$$

structure: benzyl-O—C(R_7'')=C(R_8'')—C(R_9'')... with O—O—(CH_2)_p dioxole ring

| Code Number | p | —R_9'' | Empirical Formula | Molecular Weight | Melting Point °C. | Yield % | IR or NRM spectrum or elementary analysis |
|---|---|---|---|---|---|---|---|
| | | | | | | | (J = 10Hz); 6.45,d(J = 10Hz) & 4.27,s (6 benzodioxane protons) 7.38,s & 5.12,s O—CH_2—Ph 0.8–1.9, massive COOC_5H_11n |
| 780 330 | 2 | —COO—C_6H_11 (cyclohexyl) | XI_c  C_22H_24O_5 | 368.412 | 102 | 58 | NMR (CDCl_3) δ ppm = 7.35,d (J = 10Hz); 6.45,d(J = 10Hz) & 4.3,s (6 benzodioxane protons) 7.32,s & 5.15,s O—CH_2—Ph |
| 770 202 | 2 | —CONH_2 | XI_d  C_16H_15NO_4 | 285.288 | 136 | 92 | Elementary analysis<br>      C    H    N<br>Cal. %  67.36  5.30  4.91<br>Obt. %  67.13  5.37  4.76 |
| 770 849 | 2 | —CONH—Ph | XI_d  C_22H_19NO_4 | 361.38 | 196 | 84 | NMR (DMSO) δ ppm = 7.0–7.9, massive; 6.8,d (J = 10Hz) (11 aromatic protons) 5.1, s (OCH_2—); 4.4,s (4 dioxane protons) 8.7,s: NH |
| 770 598 | 2 | —NH—CO—C_4—H_9(n) | XI_e  C_20H_23NO_4 | 341.392 | 157 | 72 | NMR (CDCl_3) δ ppm = 7.75,d (J = 10Hz); 6.47,d(10Hz) & 4.26,s (6 benzodioxane protons) 7.38,s & 5.08,s O—CH_2—Ph 2.35,m; 0.8 to 2.0, massive COC_4H_9 (n) |
| 770 689 | 2 | —NH—CO—CH(CH_3)_2 (iPr) | XI_e  C_19H_21NO_4 | 327.366 | 155 | 74 | NMR (CDCl_3) δ ppm = 7.8,d(J = 10 Hz); 6.5,d (J = 10Hz) & 4.25 s (6 benzodioxane protons) 7.35,s & 5.08,s O—CH_2—Ph 2.5,m & 1.07,d (J = 6Hz) CO—iPr 7.7,s NH |
| 770 530 | 2 | —NH—CO—C_6H_11 (cyclohexyl) | XI_e  C_22H_25NO_4 | 367.43 | 145 | 70 | NMR (CDCl_3) δ ppm = 7.82,d(J = 10 Hz); 6.50,d(J = 10Hz) & 4.3 s (6 benzodioxane protons) 7.38,s & 4.10 s O—CH_2—Ph 1.2, to 2.4, massive CO—C_6H_11 |
| 770 526 | 2 | —NH—CO—Ph | XI_e  C_22H_19NO_4 | 361.38 | 155 | 96 | NMR (CDCl_3) δ ppm = 7.9,m; 7.4m & 6.52,d(J = 10Hz) (aromatic protons) 5.08,s O—CH_2 4.22 s dioxane protons 8.20 s NH |
| 770 607 | 2 | —NH—COC_3H_7n | XI_e  C_19H_21NO_4 | 327.366 | 134.5 | 70 | NMR (CDCl_3) δ ppm = 7.75,d (J = 10Hz) 6.47,d(J = 10Hz) & 4.22,s (6 benzodioxane protons) 7.35 s & 5.08 s: O—CH_2—Ph 2.25,m; 1.70 m & 0.98,t(J = 6Hz) COC_3H_7n) |
| 770 074 | 2 | —NHCONH—CH_3 | XI_f  C_17H_18N_2O_4 | 314.330 | 220 | 98 | δ ppm = 7.30,d; 7.52,d; (J = 10Hz) & 4.20,s: (benzodioxane protons) = 7.64,s; 7.50,m; NH—CONH = 7.20,s & 5.00,s: |

TABLE III-continued

Structure (XI): $R_7'' = R_8'' = H$

Benzyl-O-substituted benzene with $R_7''$, $R_8''$, $R_9''$ substituents and O-O-(CH$_2$)$_p$ bridge.

| Code Number | p | —R$_9''$ | Empirical Formula | Molecular Weight | Melting Point °C. | Yield % | IR or NRM spectrum or elementary analysis |
|---|---|---|---|---|---|---|---|
| 780 220 | 2 | —NHCONH—C$_6$H$_4$—OCH$_3$ | XI$_f$ C$_{23}$H$_{22}$N$_2$O$_5$ | 406.422 | 240 | 89 | O—CH$_2$—C$_6$H$_5$ = 2.63,d(J = 5Hz): —CH$_3$ NMR (DMSO) δ ppm = 7.4 m; 6.7, m (aromatic protons) 5.0,s: O—CH$_2$; 4.3,s dioxane proton) 3.7,s: O—CH$_3$ 8.8 s; 8.0 s NHCONH |
| 780 406 | 1 | —NHCONHCH$_3$ | XI$_f$ C$_{16}$H$_{16}$N$_2$O$_4$ | 300.304 | 200 | 100 | (DMSO) δ ppm = 7.25,d(J = 10Hz); 6.55,d(J = 10Hz) & 5.95,s (4 benzodioxol protons) 7.40,s & 5.10,s O—CH$_2$—C$_6$H$_5$ 7.8,s & 6.15, m NHCONH 2.65,d(J = 5Hz) —CH$_3$ |
| 780 238 | 3 | —COCH$_3$ | XI$_i$ C$_{18}$H$_{18}$O$_4$ | 298.324 | 78 | 43 | Elementary analysis:           C    H<br>Cal. (%) 72.46 6.08<br>Obt. (%) 72.33 6.15 |
| 780 463 | 3 | —NHCOCH$_3$ | XI$_h$ C$_{18}$H$_{19}$NO$_4$ | 313.340 | 142 | 52 | NMR (DMSO) δ ppm = 7.38,s; 6.66, d(J = 10Hz) (aromatic protons 5.0 O—CH$_2$ 4.05,m & 2.0,s O~~O & COCH$_3$ 9.1,s NH |
| 780 465 | 3 | —NHCONHCH$_3$ | XI$_f$ C$_{18}$H$_{20}$N$_2$O$_4$ | 328.346 | 140 | 78 | Elementary analysis<br>      C    H    N<br>Cal. (%) 65.84 6.14 8.53<br>Obt. (%) 65.54 6.10 8.23 |
| 770 611 | 2 | —NH—CO+ | XI$_e$ C$_{20}$H$_{23}$NO$_4$ | 341.392 | 113 | 73 | NMR (CDCl$_3$) δ ppm = 7.8,d(J = 10Hz) 6.5 d(J = 10Hz) & 4.3 s (6 benzodioxane protons) 7.4,s & 5.1 s O—CH$_2$—C$_6$H$_5$ 1.3,s CO+ |
| 770 480 | 2 | —NHCONHC$_3$H$_7$(n) | XI$_f$ C$_{19}$H$_{22}$N$_2$O$_4$ | 342.382 | 180 | 75 | Elementary analysis<br>      C    H    N<br>Cal. (%) 66.65 6.48 8.18<br>Obt. (%) 66.28 6.49 8.27 |
| 770 627 | 2 | —NH—CO—NH—CH(CH$_3$)$_2$ | XI$_f$ C$_{19}$H$_{22}$N$_2$O$_4$ | 342.382 | 182-4 | 80 | NMR (DMSO) δ ppm = 7.35,d(J = 10Hz) ; 6.34,d(J = 10Hz) & 4.28 s (6 benzodioxane protons) 7.45,s; 5.05,s OCH$_2$—C$_6$H$_5$ 7.8,s; 6.65 m; 3.8 m; 1.1 d (J = 7Hz) NHCONH—CH(CH$_3$)$_2$ |
| 770 631 | 2 | —NHCONH—C$_4$H$_9$(n) | XI$_f$ C$_{20}$H$_{24}$N$_2$O$_4$ | 356.408 | 175-8 | 84 | NMR(DMSO) δppm = 7.5,m; 6.50 d(J = 10Hz) aromatic protons) 5.0,s: O—CH$_2$ 4.35, s: dioxane protons 3.1,m; 0.8-1.6, massive C$_4$H$_9$(n) 7.7,s; 6.7 m NHCONH |
| 770 708 | 2 | —NHCONH+ | XI$_f$ C$_{20}$H$_{24}$N$_2$O$_4$ | 356.408 | 174 | 98 | NMR(DMSO) δppm = 7.3,d(J = 10 Hz); 6.35,d(J = 10Hz) & 4.35,s (6 benzodioxane protons) 7.43,s; 5.05 s O—CH$_2$—C$_6$H$_5$ 7.62,s; 6.65,s; 1.3,s NHCONH + |

TABLE III-continued

(XI): $R_7'' = R_8'' = H$

| Code Number | p | $-R_9''$ | Empirical Formula | Molecular Weight | Melting Point °C. | Yield % | IR or NRM spectrum or elementary analysis |
|---|---|---|---|---|---|---|---|
| 770 078 | 2 | $-NH-CONH-\text{cyclohexyl}$ | XI$_f$ C$_{22}$H$_{26}$N$_2$O$_4$ | 382.444 | 225 | 94 | NMR(DMSO) δppm = 7.5,d(J = 10 Hz); 6.5,d(J = 10Hz) & 4.32,s (6 benzodioxane protons) 7.40,s; 5.0,s O—CH$_2$—phenyl 7.62,s; 6.78,s NHCONH 1.2–2.2 massive —cyclohexyl |
| 770 082 | 2 | $-NH-CONH-\text{phenyl}$ | XI$_f$ C$_{22}$H$_{20}$N$_2$O$_4$ | 376.39 | 218 | 95 | NMR (DMSO) δppm = 7.4,m; 6.60, d(J = 10Hz) aromatic protons 5.01,s: O—CH$_2$; 4.32,s dioxane protons 9.1,s; 8.0 s NHCONH |

The embodiments of the invention in which an exclusive property or privilege is claimed are defined as follows:

1. A compound having the formula

wherein n is 1, 2 or 3, and
   (A) when n is 2, R$_9$ is selected from the group consisting of methoxy, acetyl, hydroxy, acetoxy, alkoxycarbonyl in which the alkyl has 2 to 5 carbon atoms, cyclohexyloxycarbonyl, carboxamido, N-methylcarboxamido, N-cyclohexylcarboxamido, N-phenylcarboxamido, alkanoylamino in which the alkyl has 2 to 5 carbon atoms, cyclohexylcarbonylamino, benzoylamino, N-alkylcarbamoylamino in which the alkyl has 1 to 5 carbon atoms, N-cyclohexylcarbamoylamino, N-phenylcarbamoylamino, N-paramethoxyphenylcarbamoylamino, ethoxycarbonylamino, N,N'-dimethylcarbamoylamino, methylamino, morpholinocarbonylamino, N,N-dimethylcarbamoylamino, carboxamidomethyl, N-methylcarboxamidomethyl, hydroxycarbonylmethyl, cyano, ethyl acetate, carboxy, amino, hydroxymethyl, cyanomethyl, chloromethyl and acetamido, and
   (B) when n is 1 or 3, R$_9$ is selected from the group consisting of acetyl, amino, acetamido and acetyl oxime.

2. A compound according to claim 1 in which the combination of parameters n and R$_9$ is as defined in (A).

3. A compound according to claim 1 in which the combination of parameters n and R$_9$ is as defined in (B).

4. A compound according to claim 1 having the formula

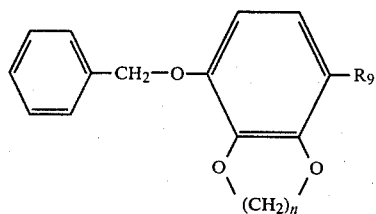

5. A compound according to claim 1 having the formula

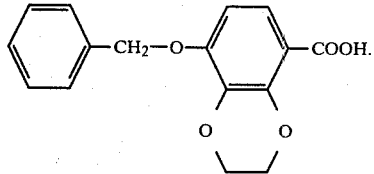

6. A compound according to claim 1 having the formula

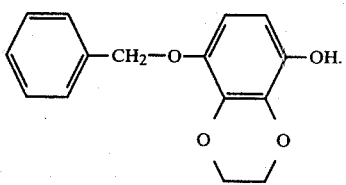

7. A compound according to claim 1 having the formula

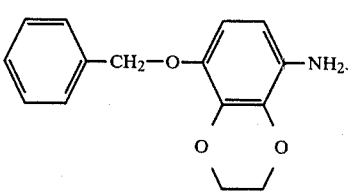

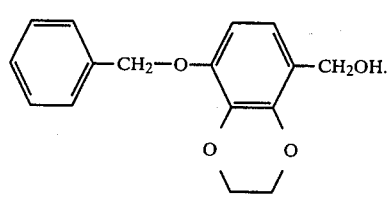
8. A compound according to claim 1 having the formula
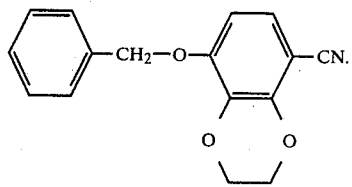
* * * * *